(12) United States Patent
Niederst et al.

(10) Patent No.: US 9,724,276 B2
(45) Date of Patent: Aug. 8, 2017

(54) DENTAL MATERIALS AND METHOD OF MANUFACTURE

(71) Applicant: Valspar Sourcing, Inc., Minneapolis, MN (US)

(72) Inventors: Jeffrey Niederst, Leechburg, PA (US); Richard H. Evans, Wexford, PA (US); Robert M. O'Brien, Monongahela, PA (US); Kevin Romagnoli, Pittsburgh, PA (US); Carl Cavallin, Needville, TX (US); T. Howard Killilea, North Oaks, MN (US); Mark S. Von Maier, Harmony, PA (US)

(73) Assignee: Valspar Sourcing, Inc., Minneapolis, MN (US)

( * ) Notice: Subject to any disclaimer, the term of this patent is extended or adjusted under 35 U.S.C. 154(b) by 3 days.

(21) Appl. No.: 14/420,036

(22) PCT Filed: Mar. 15, 2013

(86) PCT No.: PCT/US2013/032257
§ 371 (c)(1),
(2) Date: Feb. 6, 2015

(87) PCT Pub. No.: WO2014/025406
PCT Pub. Date: Feb. 13, 2014

(65) Prior Publication Data
US 2015/0224034 A1   Aug. 13, 2015

Related U.S. Application Data

(60) Provisional application No. 61/681,452, filed on Aug. 9, 2012.

(51) Int. Cl.
A61K 6/083 (2006.01)
A61K 6/00 (2006.01)
C08F 222/20 (2006.01)

(52) U.S. Cl.
CPC .............. *A61K 6/083* (2013.01); *A61K 6/005* (2013.01); *A61K 6/0058* (2013.01); *C08F 222/20* (2013.01)

(58) Field of Classification Search
CPC ..................................................... A61K 6/083
See application file for complete search history.

(56) References Cited

U.S. PATENT DOCUMENTS

| 3,085,992 A | 4/1963 | Lee et al. |
|---|---|---|
| 3,153,008 A | 10/1964 | Fox |
| 3,220,974 A | 11/1965 | Fox |
| 3,275,601 A | 9/1966 | Schnell et al. |
| 3,491,111 A | 1/1970 | Lin |
| 3,491,112 A | 1/1970 | Lin |
| 3,491,116 A | 1/1970 | Lin |
| 3,509,174 A | 4/1970 | Lin |
| 3,539,375 A | 11/1970 | Baum |
| 3,624,107 A | 11/1971 | Lin |
| 3,627,787 A | 12/1971 | Lin |
| 3,641,011 A | 2/1972 | Lin et al. |
| 3,642,828 A | 2/1972 | Farber et al. |
| 3,681,390 A | 8/1972 | Lin |
| 3,775,424 A | 11/1973 | Farber |
| 3,853,869 A | 12/1974 | Farber |
| 3,879,348 A | 4/1975 | Serini et al. |
| 3,888,812 A | 6/1975 | Plettner |
| 3,920,510 A | 11/1975 | Hatano et al. |
| 3,959,571 A | 5/1976 | Yahagi et al. |
| RE28,862 E | 6/1976 | Siemonsen et al. |
| 3,971,808 A | 7/1976 | Baumann et al. |
| 4,011,184 A | 3/1977 | van Reijendam et al. |
| 4,076,764 A | 2/1978 | Bauer |
| 4,111,910 A | 9/1978 | Baggett |
| 4,172,103 A | 10/1979 | Serini et al. |
| 4,333,809 A | 6/1982 | Schreckenberg et al. |
| 4,368,315 A | 1/1983 | Sikdar |
| 4,374,233 A | 2/1983 | Loucks et al. |
| 4,468,483 A | 8/1984 | Yeakey et al. |
| 4,510,513 A | 4/1985 | Yamaguchi et al. |
| 4,522,984 A | 6/1985 | Watanabe et al. |
| 4,564,655 A | 1/1986 | Liu |
| 4,611,036 A | 9/1986 | Sekiguchi et al. |
| 4,657,941 A | 4/1987 | Blackwell et al. |
| 4,696,955 A | 9/1987 | Kuhlmann |
| 4,729,983 A | 3/1988 | Satake et al. |
| 4,794,102 A | 12/1988 | Petersen et al. |

(Continued)

FOREIGN PATENT DOCUMENTS

| EP | 0 265 791 A2 | 5/1988 |
|---|---|---|
| EP | 0 313 862 A2 | 5/1989 |

(Continued)

OTHER PUBLICATIONS

Kim, Y.; Kim, C., K.; Cho, B., H.; Son, H., H.; Um, C., M.; Kim, O. Y. J. Biomed. Mater. Res. B Appl. Biomater. 2004, 70B, 82-90; Wiley Periodicals, Inc.*

International Search Report and Written Opinion for International Application No. PCT/US2013/032257, mailed Jul. 9, 2013. (7 pgs).

International Preliminary Report on Patentability for International Application No. PCT/US2013/032257, mailed Feb. 10, 2015. (5 pgs).

Fang, Hong, Weida Tong, Leming M. Shi, Robert Blair, Roger Perkins, William Branham, Bruce S. Hass, Qian Xie, Stacy L. Dial, Carrie L. Moland and Daniel M. Sheehan, "Structure-Activity Relationships for a Large Diverse Set of Natural, Synthetic, and Environmental Estrogens." Chem. Res. Toxicol. 2001, vol. 14, No. 3, pp. 280-294. (15 pages).

(Continued)

*Primary Examiner* — Michael Pepitone
(74) *Attorney, Agent, or Firm* — Patterson Thuente Pederson, P.A.

(57) ABSTRACT

Dental materials may be made from polyhydric phenols that are non-genotoxic and exhibit estrogenic activity less than that of bisphenol S, while exhibiting properties such as strength and flexibility comparable to those of conventional BPA-derived dental materials.

16 Claims, No Drawings

(56) References Cited

U.S. PATENT DOCUMENTS

| | | | |
|---|---|---|---|
| 4,794,156 A | 12/1988 | Ho et al. | |
| 4,816,495 A | 3/1989 | Blackwell et al. | |
| 4,849,502 A | 7/1989 | Evans et al. | |
| 4,994,217 A | 2/1991 | Banevicius et al. | |
| 5,010,147 A | 4/1991 | Westeppe et al. | |
| 5,068,284 A | 11/1991 | Ullman et al. | |
| 5,080,961 A | 1/1992 | Macy et al. | |
| 5,102,608 A | 4/1992 | Frencken et al. | |
| 5,288,839 A | 2/1994 | Greco | |
| 5,318,999 A | 6/1994 | Mitra et al. | |
| 5,446,009 A | 8/1995 | Minami et al. | |
| 5,494,950 A | 2/1996 | Asakage et al. | |
| 5,496,921 A | 3/1996 | Sakashita et al. | |
| 5,576,413 A | 11/1996 | Bussink et al. | |
| 5,591,788 A | 1/1997 | Anderson et al. | |
| 5,803,301 A | 9/1998 | Sato et al. | |
| 5,807,912 A | 9/1998 | Wu et al. | |
| 5,859,172 A | 1/1999 | Sakashita et al. | |
| 5,876,210 A | 3/1999 | Klee et al. | |
| 5,880,248 A | 3/1999 | Sakashita et al. | |
| 6,043,333 A | 3/2000 | Kuboki et al. | |
| 6,048,931 A | 4/2000 | Fujita et al. | |
| 6,060,577 A | 5/2000 | Davis | |
| 6,103,311 A | 8/2000 | Masuda et al. | |
| 6,133,402 A | 10/2000 | Coates et al. | |
| 6,184,339 B1 | 2/2001 | Stansbury et al. | |
| 6,225,436 B1 | 5/2001 | Eiffler et al. | |
| 6,399,738 B1 | 6/2002 | Ito | |
| 6,469,127 B1 | 10/2002 | Furunaga et al. | |
| 6,566,426 B1 | 5/2003 | Kanaida et al. | |
| 6,579,829 B2 | 6/2003 | Nishimura et al. | |
| 6,608,163 B2 | 8/2003 | Bailly et al. | |
| 6,660,688 B2 | 12/2003 | Yamada et al. | |
| 6,723,765 B2 | 4/2004 | Bammel | |
| 6,833,398 B2 | 12/2004 | Agarwal et al. | |
| 6,844,071 B1 | 1/2005 | Wang et al. | |
| 6,916,874 B2 | 7/2005 | Mazza et al. | |
| 6,924,328 B2 | 8/2005 | Legleiter et al. | |
| 6,984,262 B2 | 1/2006 | King et al. | |
| 6,984,608 B2 | 1/2006 | Makitalo et al. | |
| 7,022,765 B2 | 4/2006 | Adedeji et al. | |
| 7,087,705 B2 | 8/2006 | Ashtekar et al. | |
| 7,141,359 B2 | 11/2006 | Suga et al. | |
| 7,256,228 B2 | 8/2007 | Agarwal et al. | |
| 7,332,560 B2 | 2/2008 | Heuer et al. | |
| 7,635,662 B2 | 12/2009 | Kabashima et al. | |
| 7,682,674 B2 | 3/2010 | Vogt et al. | |
| 7,803,439 B2 | 9/2010 | Crawford et al. | |
| 7,803,440 B2 | 9/2010 | Crawford et al. | |
| 8,124,669 B2 | 2/2012 | Terakawa et al. | |
| 8,142,858 B2 | 3/2012 | Cooke et al. | |
| 8,353,657 B2 | 1/2013 | Lat et al. | |
| 8,795,830 B2 | 8/2014 | Wyman et al. | |
| 8,906,507 B2 | 12/2014 | Campbell et al. | |
| 9,096,772 B2 | 8/2015 | Lespinasse et al. | |
| 9,168,206 B2 | 10/2015 | Wang et al. | |
| 2003/0181628 A1 | 9/2003 | Horn et al. | |
| 2003/0203991 A1 | 10/2003 | Schottman et al. | |
| 2003/0209553 A1 | 11/2003 | Horn et al. | |
| 2004/0044101 A1 | 3/2004 | Hirose et al. | |
| 2004/0176563 A1 | 9/2004 | Shinohara et al. | |
| 2004/0220372 A1 | 11/2004 | Qi et al. | |
| 2004/0242723 A1 | 12/2004 | Jin et al. | |
| 2005/0014004 A1 | 1/2005 | King et al. | |
| 2005/0090593 A1 | 4/2005 | Heuer et al. | |
| 2005/0118526 A1 | 6/2005 | Suga et al. | |
| 2006/0025559 A1 | 2/2006 | Wehrmann et al. | |
| 2006/0052523 A1 | 3/2006 | Bushendorf et al. | |
| 2006/0134541 A1 | 6/2006 | Fuji et al. | |
| 2007/0036903 A1 | 2/2007 | Mayr et al. | |
| 2007/0087146 A1 | 4/2007 | Evans et al. | |
| 2007/0099130 A1 | 5/2007 | Takahashi et al. | |
| 2008/0246173 A1 | 10/2008 | Braidwood et al. | |
| 2008/0314500 A1 | 12/2008 | Boers et al. | |
| 2008/0319156 A1 | 12/2008 | Fischer et al. | |
| 2009/0093562 A1* | 4/2009 | Tanikawa | C08F 290/06 522/44 |
| 2009/0326107 A1 | 12/2009 | Bittner | |
| 2010/0056726 A1 | 3/2010 | Payot et al. | |
| 2010/0086716 A1 | 4/2010 | Rüdiger et al. | |
| 2010/0274043 A1* | 10/2010 | Okada | C08F 222/1006 560/194 |
| 2011/0003267 A1 | 1/2011 | Terakawa et al. | |
| 2011/0042338 A1 | 2/2011 | Pecorini et al. | |
| 2011/0160408 A1 | 6/2011 | de Brouwer et al. | |
| 2011/0275035 A1 | 11/2011 | Lu | |
| 2011/0315591 A1 | 12/2011 | Lespinasse et al. | |
| 2012/0125800 A1 | 5/2012 | Doreau et al. | |
| 2012/0172568 A1 | 7/2012 | Ueda | |
| 2012/0276315 A1 | 11/2012 | Michel et al. | |
| 2012/0276503 A1 | 11/2012 | Wang et al. | |
| 2013/0206756 A1 | 8/2013 | Niederst et al. | |
| 2013/0280455 A1 | 10/2013 | Evans et al. | |
| 2013/0316109 A1 | 11/2013 | Niederst et al. | |
| 2014/0113093 A1 | 4/2014 | Corbin et al. | |

FOREIGN PATENT DOCUMENTS

| | | |
|---|---|---|
| EP | 0185118 B1 | 9/1995 |
| JP | H07-126574 A | 5/1995 |
| JP | H07-196770 | 8/1995 |
| JP | 08-230328 | 9/1996 |
| JP | 08230328 | 10/1996 |
| JP | 2002-097250 A | 4/2002 |
| JP | 2002-138245 A | 5/2002 |
| JP | 2003-176348 A | 6/2003 |
| JP | 3 484546 B2 | 1/2004 |
| JP | 2004-10874 A | 1/2004 |
| WO | WO 95/26997 | 10/1995 |
| WO | WO 97/28905 | 8/1997 |
| WO | WO 98/50477 | 11/1998 |
| WO | WO 00/71337 A1 | 11/2000 |
| WO | WO 2007/048094 A2 | 4/2007 |
| WO | WO 2008/137562 A1 | 11/2008 |
| WO | WO 2009/015493 A1 | 2/2009 |
| WO | WO 2010/118349 A1 | 10/2010 |
| WO | WO 2010/118356 A1 | 10/2010 |
| WO | WO 2011/130671 A2 | 10/2011 |
| WO | WO 2012/109278 A2 | 8/2012 |
| WO | WO 2014/140233 A1 | 9/2014 |
| WO | WO 2014/140234 A1 | 9/2014 |

OTHER PUBLICATIONS

Current Status of Testing Methods Development for Endocrine Distrupters. 6th Meeting of the Task Force on Edocrine Distrupters Testing and Assessment (EDTA) Jun. 24-25, 2002, Tokyo, Ministry of Economy, Trade and Industry, Japan. (70 pages.

Kitamura, Shigeyuki, et al., "Comparative Study of the Endocrine-Disrupting Activity of Bisphenol A and 19 Related Compounds," Toxicological Sciences, vol. 84, 249-259 (2005), doi:10.1093/toxcie/kfi074, Advance Access publication Jan. 5, 2005 (11 pages).

Zhongguo Liu, et al., "Preparation, characterization and thermal properties of tetramethylbisphenol F exposy resin and mixed systems," Polym Int 2012; 61: 565-570, © 2011 Society of Chemical Industry, published online in Wiley Online Library: Nov. 10, 2011 (6 pages).

Hong Fang, et al., "Quantitative Comparisons of in Vitro Assays for Estrogenic Activities," Environmental Health Perspectives, vol. 108, No. 8, Aug. 2000, 723-729 (7 pages).

Dr. William Stokes, CertiChem, Inc., "Test Method Nomination: MCF-7 Cell Proliferation Assay of Estrogenic Activity," Jun. 4, 2004 (102 pages).

Claude G. Matasa, et al., "A wish list for orthodontic materials, 2005," The Orthodontic Materials Insider, Dec. 2004, vol. 16 Nr. 4 (8 pages).

G. P. Moss, Extension and Revision of the Von Baeyer System for Naming Polycyclic Compounds (Including Bycyclic Compounds), IUPAC Recommendations 1999, Pure Appl. Chem., vol. 71, No. 3, pp. 513-529, 1999 (17 pages).

Kwang-Hoon Song, et al., "Endocrine Disrupter Bisphenol A Induces Orphan Nuclear Receptor Nur77 Gene Expression and

(56) References Cited

OTHER PUBLICATIONS

Steroidogenesis in Mouse Testicular Leydig Cells," Endocrinology 143(6):2208-2215, Copyright 2002 by The Endocrine Society (8 pages).

Shigeki Kobayashi, et al., "Stereo Structure-Controlled and Electronic Structure-Controlled Estrogen-Like Chemicals to Design and Develop Non-estrogenic Bisphenol A Analogs Based on Chemical Hardness Concept," Chem. Pharm. Bull. 54(12) 1633-1638 (2006), Dec. 2006, 2006 Pharmaceutical Society of Japan (6 pages).

Nippon Kasei Chemical, "Flame Retardant Bisphenol F" (2 pages).

Eastman, "Eastman Tritan™ Copolyester—Lack of estrogen and testosterone activity," TRS-270, Apr. 2010 (3 pages).

P.Vinas et al, "Comparison of two derivatization-based methods for solid-phase microextraction-gas chromotography-mass spectrometric determination of bisphenol A, bisphenol S. and bisphenol migarted from food cans," published online Feb. 3, 2010, Springer-Verlag, 2010. (11 pages).

DYTEK® A-Amine (2014) downloaded from the Oct. 16, 2014 Internet Archives capture at https://web.archive.org/web/20141016043145/http://dytek.invista.com/Products/Amines/dytek-a-amine.

Tice, R.R. "The single cell gel/comet assay: a microgel electrophoretic technique for the detection of DNA damage and repair in individual cells." Environmental Mutagenesis, Eds. Phillips, D.H and Venitt, S. Bios Scientific, Oxford, UD, pp. 315-339 (1995).

Woo, B. et al., Melt Polycondensation of Bisphenol A Polycarbonate by a Forced Gas Sweeping Process, Ind. Eng. Chem. Res., vol. 40, No. 5, pp. 1312-1319 (2001).

Polycarbonates, $4^{th}$-5th Edition, Kirk-Othmer Encyclopedia of Chemical Technology, pp. 1-30 (2000).

Porter, D. S. et al., Hot-Fill Containers, New Tech for OPP & PET, Plastics Technology, Eastman Chemical Co., 6 pages (Dec. 2007).

Grace Darex® Packaging Technologies, A Global Partner for your global business, Product Book, 4 pages (2006).

Mendum, T. et al., "Research Letter, Concentration of bisphenol A in thermal paper", Green Chemistry Letters and Reviews, vol. 4, No. 1, pp. 81-86 (Mar. 2011).

Matsumoto, S. et al., "The crystal structure of two new developers for high-performance thermo-sensitive paper: H-bonded network in urea-urethane derivatives", Dyes and Pigments, 85, pp. 139-142 (2010).

\* cited by examiner

DENTAL MATERIALS AND METHOD OF MANUFACTURE

CROSS REFERENCE TO RELATED APPLICATION

This Application is a Section 371 National Stage Application of International Application No. PCT/US2013/032257, filed Mar. 15, 2013, published as WO 2014/025406 A1 on Feb. 13, 2014, in English, which is based on and claims the benefit of U.S. Provisional Application Ser. No. 61/681,452, filed Aug. 9, 2012, the disclosures of which are incorporated herein by reference.

FIELD

This invention relates to dental materials and dental products.

BACKGROUND

Dental materials such as composites have been used in preventing and treating dental carries and defects and otherwise maintaining dental health. Dental composites are a mixture of materials that typically include a free-radically polymerizable resin and a filler dispersed in the polymerizable resin. The resins typically are derived from bisphenol A (BPA) and contain methacrylate endgroups. Examples include bisphenol A diglycidyl dimethacrylate (Bis-GMA) and bisphenol A dimethacrylate (Bis-DMA).

SUMMARY

The present invention provides, in one aspect, a dental material comprising a filler or a free-radical polymerization initiator and a free-radically-polymerizable resin having a) at least one ethylenically unsaturated free-radically polymerizable group, more preferably an end group and b), one or more aryl or heteroaryl ring segments having an oxygen atom attached to the ring and, in some embodiments, a substituent group attached to the ring at an ortho or meta position relative to the oxygen atom, or one or more aryl or heteroaryl rings joined by a polar linking group or by a linking group having a molecular weight of at least 125 Daltons; and in some embodiments where both the substituent groups and the polar linking groups are or included; the resin being substantially free of bound or mobile polyhydric phenols having estrogenic activity greater than or equal to that of bisphenol S.

The present invention provides, in another aspect, a dental material comprising a filler or a polymerization initiator and a free-radically polymerizable resin comprising segments of the structure shown in Formula I:

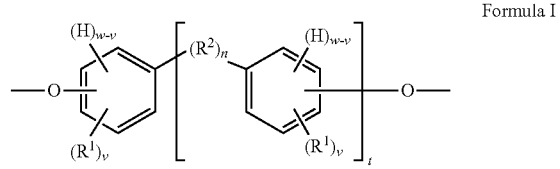

Formula I wherein:
H denotes a hydrogen atom, if present;
each $R^1$ is independently an atom or group preferably having an atomic weight of at least 15 Daltons, wherein each of the phenylene groups depicted in Formula I preferably includes at least one $R^1$ group attached to the phenylene ring at an ortho or meta position relative to the oxygen atom;
v is independently 0 to 4, more preferably 1 to 4, even more preferably 2 to 4; with the proviso that if v is 0, then n is 1 or the phenylene groups depicted in Formula I join to form a fused ring system;
w is 4;
$R^2$, if present, is preferably a divalent group;
n is 0 or 1, with the proviso that if n is 0, the phenylene rings depicted in Formula I can optionally join to form a fused ring system with each other (e.g., a substituted naphthalene group), in which case w is 3 (as opposed to 4) and v is 0 to 3 (as opposed to 0 to 4);
t is 0 or 1;
if v is 0, t is 1 then $R^2$ is a polar linking group or a linking group having a molecular weight of at least 125 Daltons;
two or more $R^1$ or $R^2$ groups can join to form one or more cyclic groups, and
the polymerizable resin includes at least one and preferably two free-radically polymerizable groups, which are preferably end groups and wherein the composition is substantially free of polyhydric phenols having estrogenic activity greater than or equal to that of bisphenol S.

When t is 1, the segment of Formula I is a segment of the below Formula IA.

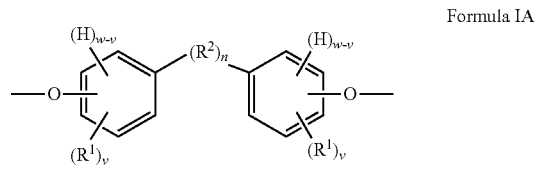

Formula IA

When t is 0, the segment of Formula I is a segment of the below Formula IB:

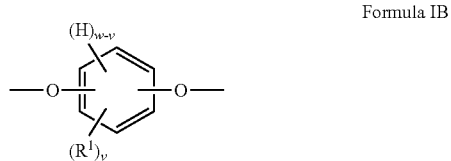

Formula IB

The present invention provides, in another aspect, a method of making a dental material, comprising:
mixing a filler or a polymerization initiator and a free-radically polymerizable resin, the resin comprising segments shown in Formula I wherein H, $R^1$, $R^2$, v, w, n and t are as described for Formula I above.

DEFINITIONS

As used herein, "a," "an," "the," "at least one," and "one or more" are used interchangeably. Thus, for example, a dental material that includes "a" resin means that the dental material can include "one or more" resins.

The term "aryl group" (e.g., an arylene group) refers to a closed aromatic ring or ring system such as phenylene, naphthylene, biphenylene, fluorenylene, and indenyl, as well as heteroarylene groups (e.g., a closed aromatic or aromaticlike ring hydrocarbon or ring system in which one or more of the atoms in the ring is an element other than carbon (e.g., nitrogen, oxygen, sulfur, and the like.). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on. When such groups are divalent, they are typically referred to as "arylene" or "heteroarylene" groups (e.g., furylene, pyridylene, and the like).

The terms "comprises" and variations thereof do not have a limiting meaning where these terms appear in the description and claims.

The term "crosslinker" refers to a molecule capable of forming a covalent linkage between polymers or between two different regions of the same polymer.

The terms "dental composition" or "dental material" are used interchangeably and include composites, sealers, cements, restoratives, bonding agents, luting agents, bases, liners and the like. A composite is a highly filled paste suitable for filling substantial voids in tooth structure. Dental cements are somewhat less highly filled and less viscous materials than composites, and typically act as a bonding agent for additional materials. Dental sealants typically containing a polymerization initiator, resin, one or more pigments, and no or low filler content.

The terms "estrogenic activity" or "estrogenic agonist" activity refer to the ability of a compound to mimic hormone-like activity through interaction with an endogenous estrogen receptor, typically an endogenous human estrogen receptor.

Organic groups in the disclosed resins may be unsubstituted or substituted. As a means of simplifying the discussion and recitation of certain terminology used throughout this application, the terms "group" and "moiety" are used to differentiate between chemical species that allow for substitution or that may be substituted and those that do not allow or may not be so substituted. Thus, when the term "group" is used to describe a chemical substituent, the described chemical material includes the unsubstituted group and that group with O, N, Si, or S atoms, for example, in the chain (as in an alkoxy group) as well as carbonyl groups or other conventional substitution. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, t-butyl, and the like, but also alkyl substituents bearing further substituents known in the art, such as hydroxy, alkoxy, alkylsulfonyl, halogen atoms, cyano, nitro, amino, carboxyl, and the like. Thus, "alkyl group" includes ether, haloalkyl, nitroalkyl, carboxyalkyl, hydroxyalkyl, sulfoalkyl, and like groups. On the other hand, the phrase "alkyl moiety" is limited to the inclusion of only pure open chain saturated hydrocarbon alkyl substituents, such as methyl, ethyl, propyl, t-butyl, and the like. As used herein, the term "group" is intended to be a recitation of both the particular moiety, as well as a recitation of the broader class of substituted and unsubstituted structures that includes the moiety. A group that may be the same or different is referred to as being "independently" something.

The term "(meth)acrylic acid" includes either or both of acrylic acid and methacrylic acid, and the term "(meth)acrylate" includes either or both of an acrylate and a methacrylate.

The term "mobile" when used with respect to a compound means that the compound can be extracted from a cured composition when the cured composition is exposed to a test medium for some defined set of conditions, depending on the end use. An example of these testing conditions is exposure of a cured dental material to HPLC-grade acetonitrile for 24 hours at 25° C.

As used herein, the term "organic group" means a hydrocarbon group (with optional elements other than carbon and hydrogen, such as oxygen, nitrogen, sulfur, and silicon) that is classified as an aliphatic group, a cyclic group, or combination of aliphatic and cyclic groups (e.g., alkaryl and aralkyl groups). The term "cyclic group" means a closed ring hydrocarbon group that is classified as an alicyclic group or an aromatic group, both of which can include heteroatoms. The term "alicyclic group" means a cyclic hydrocarbon group having properties resembling those of aliphatic groups.

The term "phenylene" as used herein refers to a six-carbon atom aryl ring (e.g., as in a benzene group) that can have any substituent groups (including, e.g., hydrogen atoms, halogens, hydrocarbon groups, oxygen atoms, hydroxyl groups, and the like). Thus, for example, the following aryl groups are each phenylene rings: $—C_6H_4—$, $—C_6H_3(CH_3)—$, and $—C_6H(CH_3)_2Cl—$. In addition, for example, each of the aryl rings of a naphthalene group are phenylene rings.

The term "polyhydric phenol" as used herein refers broadly to any compound having one or more aryl or heteroaryl groups (more typically one or more phenylene groups) and at least two hydroxyl groups attached to a same or different aryl or heteroaryl ring. Thus, for example, both hydroquinone and 4,4'-biphenol are considered to be polyhydric phenols. As used herein, polyhydric phenols typically have six carbon atoms in an aryl ring, although it is contemplated that aryl or heteroaryl groups having rings of other sizes may be used.

The terms "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "substantially free" when used with respect to a dental material that may contain a particular mobile compound means that the recited free radically polymerizable resin or cured polymer thereof contains less than 1,000 parts per million (ppm) of the recited mobile compound. The term "essentially free" when used with respect to a dental material that may contain a particular mobile compound means that the recited free radically polymerizable resin or cured polymer thereof contains less than 100 parts per million (ppm) of the recited mobile compound. The term "essentially completely free" when used with respect to a dental material that may contain a particular mobile compound means that the recited free radically polymerizable resin or cured polymer thereof contains less than 5 parts per million (ppm) of the recited mobile compound. The term "completely free" when used with respect to a dental material that may contain a particular compound means that the recited free radically polymerizable resin or cured polymer thereof contains less than 20 parts per billion (ppb) of the recited mobile compound. If the aforementioned phrases are used without the term "mobile" (e.g., "substantially free of BPA") then the recited dental material or composition contains less than the aforementioned amount of the compound whether the compound is mobile in the composition or bound to a constituent of the composition.

Also herein, the recitations of numerical ranges by endpoints include all numbers subsumed within that range (e.g., 1 to 5 includes 1, 1.5, 2, 2.75, 3, 3.80, 4, 5, and the like). Furthermore, disclosure of a range includes disclosure of all subranges included within the broader range (e.g., 1 to 5 discloses 1 to 4, 1.5 to 4.5, 4 to 5, and the like).

DETAILED DESCRIPTION

The disclosed dental materials include a filler or a polymerization initiator or both, and a free-radically polymerizable resin. Exemplary fillers may be selected from a variety of materials suitable for incorporation in compositions used for dental applications. The filler is finely divided and preferably has a maximum particle diameter less than about 50 micrometers and an average particle diameter less than about 10 micrometers as measured using, for example, a sedimentation analyzer. The filler can have a unimodal or polymodal (e.g., bimodal) particle size distribution. The filler can be an inorganic material. It can also be a crosslinked organic material that is insoluble in the polymerizable resin, and is optionally filled with inorganic filler. The filler should preferably be non-toxic and suitable for use in the mouth. The filler can be radiopaque, radiolucent or non-radiopaque.

Optionally, the surface of the filler particles may be treated with a surface treatment, such as a silane coupling agent, in order to enhance the bond between the filler and the polymerizable resin. The coupling agent may be functionalized with reactive curing groups, such as acrylates, methacrylates, and the like.

Examples of suitable inorganic fillers are naturally-occurring or synthetic materials such as quartz, nitrides (e.g., silicon nitride), glasses (including borosilicate glasses, zinc glasses, and glasses derived from, for example, Ce, Sb, Sn, Zr, Sr, Ba or Al), feldspar, kaolin, talc, titania, and zirconia-silica fillers; low Mohs hardness fillers such as those described in U.S. Pat. No. 4,695,251; and submicron silica particles (e.g., colloidal silica, and pyrogenic silicas such as the "AEROSIL" Series "OX 50", "130", "150" and "200" silicas sold by Degussa and "CAB-O-SIL M5" silica sold by Cabot Corp.). Examples of suitable organic filler particles include filled or unfilled pulverized polycarbonates, polyepoxides, and the like. Preferred filler particles are quartz, submicron silica, and non-vitreous microparticles of the type described in U.S. Pat. No. 4,503,169. Mixtures of these fillers are also contemplated, as well as combination fillers made from organic and inorganic materials. Fluoroaluminosilicate glass fillers, either untreated or silanol treated, may also be used. These glasses have the added benefit of releasing fluoride at the site of dental work when placed in the oral environment.

Typically, filler particles may be present in filler-containing dental materials in amounts from about 10 weight percent to about 90 weight percent, about 20 weight percent to about 80 weight percent or from about 30 weight percent to about 70 weight percent, based on the total dental material weight.

The disclosed dental materials may be hardened or cured by any appropriate system for curing free-radically polymerizable materials. Preferred such systems include photoinitiator systems and redox cure systems. Redox cure systems are sometimes called "chemical" cure systems because curing may occur without exposure to light or heat.

The photoinitiator preferably should be capable of promoting free-radical crosslinking of an ethylenically unsaturated moiety on exposure to light of a suitable wavelength and intensity. Visible light photoinitiators are preferred. The photoinitiator preferably is soluble in the resin. The photoinitiator may, for example, be used alone in a one-part-paste, light-cure composition, or in combination with a peroxide-containing paste in a two-part, paste-paste chemically cured system having two modes of cure (a photoinitated cure and a "dark" chemically initiated cure). In other embodiments, photoinitiator need not be employed, and the dental material could be provided as, for example, a chemically cured two-part system.

Preferred visible light-induced photoinitiators include camphorquinone (which typically is used together with a suitable hydrogen donor such as an amine), diaryliodonium simple or metal complex salts, chromophore-substituted halomethyl-s-triazines and halomethyl oxadiazoles. Particularly preferred visible light-induced photoinitiators include combinations of an alpha-diketone (e.g., camphorquinone), a diaryliodonium salt, (e.g., diphenyliodonium chloride, bromide, iodide or hexafluorophosphate), and a hydrogen donor (e.g., an amine or amine alcohol).

Preferred ultraviolet light-induced polymerization initiators include ketones such as benzyl and benzoin, and acyloins and acyloin ethers. Preferred commercially available ultraviolet light-induced polymerization initiators include 2,2-dimethoxy-2-phenylacetophenone ("IRGACURE 651") and benzoin methyl ether (2-methoxy-2-phenylacetophenone), both from Ciba-Geigy Corp.

The photoinitiator should be present in an amount sufficient to provide the desired rate of photopolymerization. This amount will be dependent in part on the light source, the thickness of the layer to be exposed to radiant energy, the filler amount, if any, in the dental material and the photoinitiator extinction coefficient. Typically, the photoinitiator will be present at a total weight of about 0.01 weight percent to about 5 weight percent, more preferably from about 0.03 weight percent to about 0.1 weight percent, based on the total dental material weight.

Dental polymerizable resins have traditionally contained BPA derivatives, derived from monomers such as 2,2-bis[4-(2-hydroxy-3-methacryloyloxy-propoxy)phenyl]propane (Bis-GMA); 2,2-bis(4-methacryloyloxy-phenyl)propane (Bis-DMA); 2,2-bis[4-(2-methacryloyloxy-ethoxy)phenyl] propane (EBPADMA); and 2,2-bis[4-glycidyl-phenyl]propane (BADGE), and include those shown in U.S. Pat. No. 3,066,112 (Bowen) and in U.S. Patent Application Publication Nos. US 2006/0009540 A1 (Jia et al.) and US 2011/0144230 A1 (Koltisko et al.). These resins when cured in formulated dental products desirably have properties including good durability, good chemical resistance and realistic optical properties.

The disclosed dental materials provide effective substitutes for BPA-derived dental materials. The disclosed free-radically polymerizable resins may be made by replacing BPA or BPA-derived monomers as used in conventional dental resins with the polyhydric phenols and polyhydric phenol-derived monomers discussed herein. The resins may be present in the disclosed dental materials in amounts from about 5 weight percent to about 95 weight percent, from about 5 weight percent to about 70 weight percent or from about 5 weight percent to about 60 weight percent, based on the total dental material weight.

The disclosed free-radically polymerizable resins preferably do not include any structural units derived from or derivable from the polyhydric phenols bisphenol A ("BPA"), bisphenol F ("BPF") or bisphenol S ("BPS"), and preferably do not include any structural units derived from or derivable from a reaction of such polyhydric phenols with a diepoxide (e.g., structural units derived from BADGE). More preferably, the resin does not include any structural units derived from or derivable from a polyhydric phenol having estrogenic agonist activity greater than or equal to that of BPS. Even more preferably, the resin does not include (e.g., is substantially free or completely free of) any structural units derived from or derivable from a polyhydric phenol having estrogenic agonist activity greater than 4,4'-(propane-2,2-diyl)bis(2,6-dibromophenol). Optimally, the resin does not include any structural units derived from or derivable from a polyhydric phenol, having estrogenic agonist activity greater than 2,2-bis(4-hydroxyphenyl)propanoic acid.

While not intending to be bound by theory, it is believed that a polyhydric phenol is less likely to exhibit any appreciable estrogenic agonist activity if the compound's chemical structure is sufficiently different from compounds having estrogenic activity such as diethylstilbestrol. The structures of preferred polyhydric phenol compounds, as will be discussed herein, are sufficiently different such that the compounds do not bind and activate a human receptor. These preferred compounds are, in some instances, at least about 6 or more orders of magnitude less active than diethylstilbestrol (e.g., when assessing estrogenic agonist effect using an in vitro assay such as the MCF-7 cell proliferation assay discussed later herein). Without being bound by theory, it is believed that such desirable structural dissimilarity can be introduced via one or more structural features, including any suitable combination thereof. For example, it is believed that one or more of the following structural characteristics can be used to achieve such structural dissimilarity:

steric hinderance (e.g., relative to one or more hydroxyl phenols), molecular weight that is arranged in three-dimensional space such that: (i) the compound does not fit, or does not readily fit, in the active site of a human estrogen receptor or (ii) the structural configuration interferes with activation of the human estrogen receptor once inside the active site, and the presence of polar groups.

In one embodiment, the free radically polymerizable resin includes one or more segments of Formula I above:

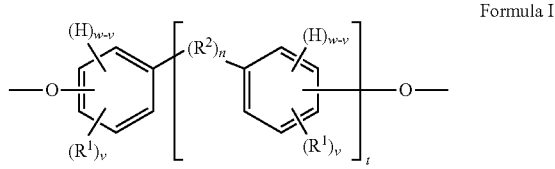

Formula I

When t is 1, the segment of Formula I is a segment of the below Formula IA:

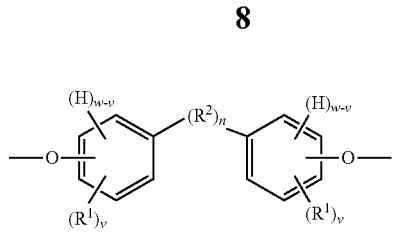

Formula IA

When t is 0, the segment of Formula I is a segment of the below Formula IB:

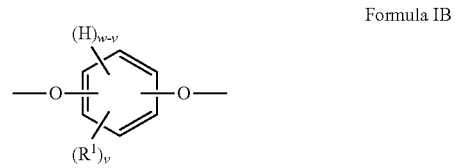

Formula IB

As depicted in the above Formula I, the segment includes at least two phenylene groups when t is 1 (illustrated in Formula IA), and includes at least one phenylene group when t is 0 (illustrated in Formula IB). The segments of each of Formulas IA and IB may optionally include one or more additional phenylene or other aryl or heteroaryl groups in addition to those depicted. Although aryl groups having a six-carbon aromatic ring are presently preferred, it is contemplated that any other suitable aryl or heteroaryl groups may be used in place of the phenylene groups depicted in Formula I, with appropriate adjustment in the allowable values for w and v. As depicted in the above Formula I, the substituent groups (e.g., —O—, H, $R^1$, and $R^2$) of each phenylene group can be located at any position on the phenylene ring relative to one another, although in certain preferred embodiments at least one $R^1$ is positioned on the ring immediately adjacent to the oxygen atom. In other embodiments in which other aryl or heteroarylene group(s) are used in place of the depicted phenylene group(s) in Formula I, it is contemplated that the same would hold true for the substituent groups of such other aryl or heteroarylene group(s).

In preferred embodiments, $R^1$ is preferably located at an ortho position on the ring relative to the oxygen atom. In some embodiments, an $R^1$ is located at each ortho position on the ring relative to the oxygen atom. While not intending to be bound by theory, it is believed that the positioning of one or more $R^1$ groups at an ortho position relative to the oxygen atom depicted in Formula I may be beneficial in reducing or eliminating estrogenic agonist activity. The benefits of $R^1$ with regards to an absence of appreciable estrogenic activity with respect to when these components are mobile are discussed in greater detail below.

In another embodiment, the one or more hydroxyl groups present on each aryl ring of a polyhydric phenol compound (for example, the phenol hydroxyl groups of a bisphenol made by protonating the oxygen atoms shown in Formula I) are sterically hindered by one or more other substituents of the aryl ring, as compared to a similar polyhydric phenol compound having hydrogen atoms present at each ortho or meta position. It is believed that it may be preferable to have substituent groups positioned at each ortho position relative to the aforementioned hydroxyl groups to provide optimal steric effect. It is believed that the steric hindrance can prevent or limit the ability of a polyhydric phenol compound to act as an agonist for a human estrogen receptor.

Preferred R¹ groups are sufficiently "bulky" to provide a suitable level of steric hindrance for the aforementioned hydroxyl groups to achieve the desired effect. To avoid any ambiguity, the term "group" when used in the context of R¹ groups refers to both single atoms (e.g., a halogen atom) or molecules (e.g., two or more atoms). The optimal chemical constituents, size, or configuration (e.g., linear, branched, etc.) of the one or more R¹ groups may depend on a variety of factors, including, for example, the location of the R¹ group on the aryl group.

Certain preferred segments of Formula I include up to four R¹ groups having an atomic weight of at least 15 Daltons. In some embodiments, the segments of Formula I include up to four R¹ groups having an atomic weight of at least 25, at least 40, or at least 50 Daltons. While the maximum suitable size of R¹ is not particularly limited, typically it will be less than 500 Daltons, more typically less than 100 Daltons, and even more typically less than 60 Daltons. Non-limiting examples of R¹ groups include groups having at least one carbon atom (e.g., organic groups), halogen atoms, sulfur-containing groups.

In presently preferred embodiments, the R¹ groups of each phenylene group, if present, preferably include at least one carbon atom, more preferably 1 to 10 carbon atoms, and even more preferably 1 to 4 carbon atoms. R¹ will typically be a saturated or unsaturated hydrocarbon group, more typically saturated, that may optionally include one or more heteroatoms other than carbon or hydrogen atoms (e.g., N, O, S, Si, a halogen atom, etc.). Examples of suitable hydrocarbon groups may include substituted or unsubstituted alkyl groups (e.g., methyl, ethyl, propyl, butyl, etc., including isomers thereof), alkenyl groups, alkynyl groups, alicyclic groups, aryl groups, or combinations thereof.

In certain preferred embodiments, each phenylene group depicted in Formula I includes at least one alkyl R¹ group. As discussed above, any suitable isomer may be used. Thus, for example, a linear butyl group may be used or a branched isomer such as an isobutyl group or a tert-butyl group. In one embodiment, a tert-butyl group (and more preferably a tert-butyl moiety) is a preferred R¹ group.

As previously mentioned, it is contemplated that R¹ may include one or more cyclic groups. In addition, R¹ may form a cyclic or polycyclic group with one or more other R¹ groups or R².

In some embodiments, one or both phenylene groups depicted in Formula I include an R¹ group that is a halogen atom located ortho to the oxygen, more preferably a higher molecular weight halogen such as bromine or iodine. However, in preferred embodiments, the segment of Formula I does not include any halogen atoms.

In some embodiments, a suitable R¹ group is selected and positioned at the ortho position such that a width "f" measured perpendicular from a centerline of the phenylene group (or other suitable aryl group) to the maximal outside extent of the van der Waals volume of R¹ (corresponding to the radius of the van der Waals radius of R¹) is greater than about 4.5 Angstroms. This width measurement may be determined via theoretical calculation using suitable molecular modeling software and is illustrated below.

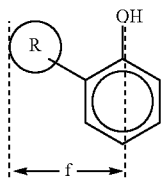

As illustrated above, the centerline for the depicted phenylene group includes the carbon atom to which the phenol hydroxyl group attaches and the para carbon atom. For example, While not intending to be bound by theory, it is believed that it is generally desirable that f be greater than about 4.5 Angstroms if R² is a —C(CH₃)₂- group. In some embodiments, R¹ may be selected and positioned at an ortho position such that f is less than about 4.5 Angstroms. For example, if R² is a methylene bridge (—CH₂—), in some embodiments R¹ can be selected and positioned such that f is less than about 4.5 Angstroms, which is believed to be the case for certain preferred segments of Formula I derived from, e.g., 4,4'-methylenebis(2,6-dimethylphenol).

R² is present or absent in the segment of Formula IA depending on whether n is 0 or 1. When R² is absent in the segment of Formula IA, either (i) a carbon atom of one phenylene ring is covalently attached to a carbon atom of the other phenylene ring (which occurs when w is 4) or (ii) the phenylene groups depicted in Formula IA join to form a fused ring system (which occurs when w is 3 and the two phenylene groups are so fused). In some embodiments, R² (or the ring-ring covalent linkage if R² is absent) is preferably attached to at least one, and more preferably both, phenylene rings at a para position (e.g., a 1,4-position) relative to the oxygen atom depicted in Formula IA. An embodiment of the segment of Formula IA, in which n is 0, w is 3, and v is independently 0 to 3 such that the two phenylene groups have joined to form a naphthalene group, is depicted below:

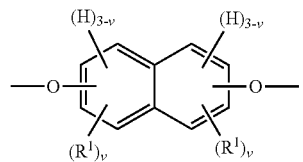

R² can be any suitable divalent group including, for example, carbon-containing groups (which may optionally include heteroatoms such as, e.g., N, O, P, S, Si, a halogen atom, etc.), sulfur-containing groups (including, e.g., a sulfur atom, a sulfinyl group —S(O)—, a sulfonyl group —S(O₂)—, etc.), oxygen-containing groups (including, e.g., an oxygen atom, a ketone group, etc.), nitrogen-containing groups, or a combination thereof. In embodiments in which v in Formula(I) is zero, R² preferably is a polar linking group or a linking group having a molecular weight of at least 125 Daltons.

In preferred embodiments of the segment of Formula IA, R² is present and is typically an organic group containing less than about 15 carbon atoms, and even more typically 1 or 4-15 carbon atoms. In some embodiments, R² includes 8 or more carbon atoms. R² will typically be a saturated or unsaturated hydrocarbon group, more typically a saturated divalent alkyl group, and most preferably an alkyl group that does not constrain the movement of the connected phenylene groups in an orientation similar to that of diethylstilbestrol or dienestrol. In some embodiments, R² may include one or more cyclic groups, which may be aromatic or alicyclic and can optionally include heteroatoms. The one or more optional cyclic groups of R² can be present, for example, (i) in a chain connecting the two phenylene groups depicted in Formula IA, (ii) in a pendant group attached to a chain connecting the two phenylene groups, or both (i) and (ii).

The atomic weight of the $R^2$ group, if present, may be any suitable atomic weight. Typically, however, $R^2$ has an atomic weight of less than about 500 Daltons, less than about 400 Daltons, less than 300 Daltons, or less than 250 Daltons.

In some embodiments, $R^2$ includes a carbon atom that is attached to a carbon atom of each of the phenylene groups depicted in Formula I. For example, $R^2$ can have a structure of the formula —C($R^7$)($R^8$)—, wherein $R^7$ and $R^8$ are each independently a hydrogen atom, a halogen atom, an organic group, a sulfur-containing group or a nitrogen-containing group, and wherein $R^7$ and $R^8$ can optionally join to form a cyclic group. In some embodiments, at least one of $R^7$ and $R^8$ is a hydrogen atom, and more preferably both. In one preferred embodiment, $R^2$ is a divalent methylene group (—$CH_2$—). While not intending to be bound by theory, it is believed that it may be generally desirable to avoid using an $R^2$ group wherein each of $R^7$ and $R^8$ are methyl (—$CH_3$) groups. It may also be generally desirable to avoid using an $R^2$ group in which $R^7$ and $R^8$ join to form a monocyclic cyclohexyl group.

It is also thought to be generally desirable to avoid using either of the following "constrained" unsaturated structures (i) or (ii) as $R^2$: (i) —C($R^9$)=C($R^9$)— or (ii) C(=C($R^{10}$)$_y$)—C(=C($R^{10}$)$_y$)—, wherein y is 1 or 2 and each of $R^9$ or $R^{10}$ is independently a hydrogen atom, a halogen atom, an organic group, or a monovalent group. For example, the following unsaturated structures (i) and (ii) are preferably avoided: (i) —C($CH_2CH_3$)=C($CH_2CH_3$)— and (ii) —C(=$CHCH_3$)—C(=$CHCH_3$)—.

While not intending to be bound by theory it is believed that a suitably low atomic weight $R^2$ group such as, e.g., —$CH_2$— (14 Daltons), can help avoid estrogenic activity. In some embodiments where $R^2$ is a —C($R^7$)($R^8$)— group, it may be desirable that $R^2$ have an atomic weight of less than 42 Daltons or less than 28 Daltons. It is also believed that a suitably high atomic weight $R^2$ can also help interfere with the ability of a polyhydric phenol to function as an agonist for a human estrogen receptor. In some embodiments where $R^2$ is a —C($R^7$)($R^8$)— group, it may be desirable that $R^2$ have an atomic weight that is greater than about 125, 150, 175, or 200 Daltons. By way of example, a diphenol compound has been determined to be appreciably non-estrogenic that: (a) is not "hindered" (the phenol hydroxyl groups are not surrounded by ortho hydrogens) and (b) has an $R^2$ group in the form of —C($R^7$)($R^8$)— having an atomic weight greater than 200 Daltons.

While not intending to be bound by theory, preferred $R^2$ groups include divalent groups that promote that the orientation of a polyhydric phenol compound in a three-dimensional configuration that is sufficiently different from 17β-estradiol or other compounds (e.g., diethylstilbestrol) having estrogenic activity. For example, while not intending to be bound by theory, it is believed that the presence of $R^2$ as an unsubstituted methylene bridge (—$CH_2$—) can contribute to the reduction or elimination of estrogenic activity. It is also contemplated that a singly substituted methylene bridge having one hydrogen attached to the central carbon atom of the methylene bridge (—C($R^7$)(H)—; see, e.g. the $R^2$ group of 4,4'Butylidenebis(2-t-butyl-5-methylphenol)) may also contribute such a beneficial effect, albeit perhaps to a lesser extent.

In some embodiments, $R^2$ is of the formula —C($R^7$)($R^8$)— wherein $R^7$ and $R^8$ form a ring together that includes one or more heteroatoms. In one such embodiment, the ring formed by $R^7$ and $R^8$ further includes one or more additional cyclic groups such as, e.g., one or more aryl cyclic groups (e.g., two phenylene rings).

In one embodiment, $R^2$ is of the formula —C($R^7$)($R^8$)— wherein at least one of $R^7$ and $R^8$ form a ring with an $R^1$ of the depicted phenylene group. In one such embodiment, each of $R^7$ and $R^8$ forms such a ring with a different depicted phenylene group.

The oxygen atom of a phenylene ring depicted in Formula I can be positioned on the ring at any position relative to $R^2$ (or relative to the other phenylene ring if $R^2$ is absent). In some embodiments, the oxygen atom (which is preferably an ether oxygen) and $R^2$ are located at para positions relative to one another. In other embodiments, the oxygen atom and $R^2$ may be located ortho or meta to one another.

In some embodiments, the substituted phenylene groups of Formula IA are symmetric relative to one another. Stated otherwise, the substituted phenylene groups are preferably formed from the same phenol compound, thereby resulting in the same substituent groups on each ring located at the same ring positions. An example of a compound having symmetric phenylene groups is provided below.

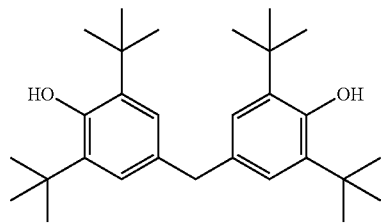 [SMILES: CC(C)(C)c1cc(Cc2cc(C(C)(C)C)c(O)c(C(C)(C)C)c2)cc(C(C)(C)C)c1O]

An example of a compound having phenylene groups that are not symmetric is provided below, in which a methyl group is at a meta position on one ring and at an ortho position on the other.

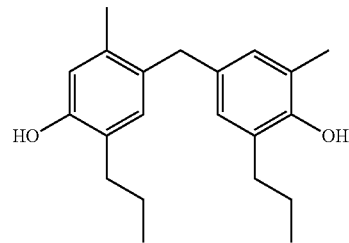 [SMILES: CCCc1cc(Cc2cc(C)c(O)c(CCC)c2)c(C)cc1O]

Shown below in Formula II is a polyhydric phenol compound that does not exhibit appreciable estrogenic activity. $R^1$, $R^2$, n, t, v, and w are as described in Formula I:

Formula II

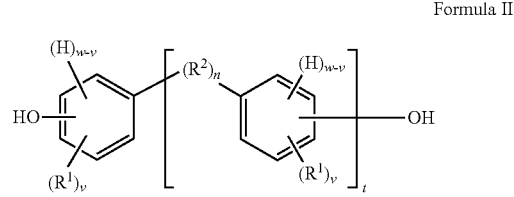

When t is 1, the compound of Formula II is of the below Formula IIA:

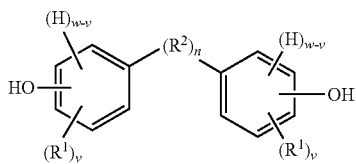

Formula IIA

When t is 0, the compound of Formula II is of the below Formula IIB:

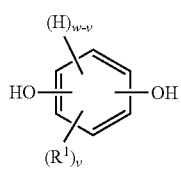

Formula IIB

Preferred appreciably non-estrogenic compounds exhibit a degree of estrogen agonist activity, in a competent in vitro human estrogen receptor assay, that is preferably less than that exhibited by 4,4'-(propane-2,2-diyl)diphenol in the assay, even more preferably less than that exhibited by bisphenol S in the assay, even more preferably less than that exhibited by 4,4'-(propane-2,2-diyl)bis(2,6-dibromophenol) in the assay, and optimally less than about that exhibited by 2,2-bis(4-hydroxyphenyl)propanoic acid in the assay. It has been found that compounds such as 4,4'-methylenebis(2,6-di-t-butylphenol), 2,2'-methylenebis(4-methyl-6-t-butylphenol), 4,4'-methylenebis(2,6-dimethylphenol), 4,4'butylidenebis(2-t-butyl-5-methylphenol), and 2,5-di-t-butylhydroquinone do not exhibit appreciable estrogenic activity in a suitable in vitro assay whose results are known to be directly correlated to the results of the MCF-7 cell proliferation assay ("MCF-7 assay") through analysis of common reference compounds.

The MCF-7 assay is a useful test for assessing whether a polyhydric phenol compound is appreciably non-estrogenic. The MCF-7 assay uses MCF-7, clone WS8, cells to measure whether and to what extent a substance induces cell proliferation via estrogen receptor (ER)-mediated pathways. The method is described in "Test Method Nomination: MCF-7 Cell Proliferation Assay of Estrogenic Activity" submitted for validation by CertiChem, Inc. to the National Toxicology Program Interagency Center for the Evaluation of Alternative Toxicological Methods (NICEATM) on Jan. 19, 2006 (available online at iccvam.niehs.nih gov/methods/endocrine/endodocs/SubmDoc.pdf).

A brief summary of the method of the aforementioned MCF-7 assay is provided below. MCF-7, clone WS8, cells are maintained at 37° C. in RMPI (or Roswell Park Memorial Institute medium) containing Phenol Red (e.g., GIBCO Catalog Number 11875119) and supplemented with the indicated additives for routine culture. An aliquot of cells maintained at 37° C. are grown for two days in phenol-free media containing 5% charcoal stripped fetal bovine serum in a 25 cm$^2$ tissue culture flask. Using a robotic dispenser such as an EPMOTION™ 5070 unit from Eppendorf AG, MCF-7 cells are seeded at 400 cells per well in 0.2 ml of hormone-free culture medium in Corning 96-well plates. The cells are adapted for 3 days in the hormone-free culture medium prior to adding the chemical to be assayed for estrogenic activity. The media containing the test chemical is replaced daily for 6 days. At the end of a 7 day exposure to the test chemical, the media is removed, the wells are washed once with 0.2 ml of HBSS (Hanks' Balanced Salt Solution), and then assayed to quantify amounts of DNA per well using a micro-plate modification of the Burton diphenylamine (DPA) assay, which is used to calculate the level of cell proliferation.

Examples of appreciably non-estrogenic polyhydric phenols include polyhydric phenols that when tested using the MCF-7 assay, exhibit a Relative Proliferative Effect ("RPE") having a logarithmic value (with base 10) of less than about −2.0, more preferably an RPE of-3 or less, and even more preferably an RPE of −4 or less. RPE is the ratio between the EC50 of the test chemical and the EC50 of the control substance 17-beta estradiol times 100, where EC50 is "effective concentration 50%" or half-maximum stimulation concentration for cell proliferation measured as total DNA in the MCF-7 assay.

Table 1 shown below includes exemplary preferred polyhydric phenol compounds of Formula II and their expected or measured logarithmic RPE values in the MCF-7 assay.

TABLE 1

| Polyhydric Compound of Formula II | Structure | Reference Compound | Log RPE |
|---|---|---|---|
| | | 17β-estradiol | 2.00 |
| | | diethylstilbestrol | about 2 |
| | | dienestrol | about 2 |
| | | Genistein | −2 |
| | | Bisphenol S | −2 |
| | | Bisphenol F | −2 |
| 4,4'-isopropylidenebis(2,6-dimethylphenol) | 1 | | −2 |
| 4,4'-(propane-2,2-diyl)bis(2,6-dibromophenol) | 16 | | −3 |
| 4,4'-(ethane-1,2-diyl)bis(2,6-dimethylphenol) | 2 | | −3 |
| 4,4',4''-(ethane-1,1,1-triyl)triphenol | 3 | | −3 |
| 4,4'-(1-phenylethane-1,1-diyl)diphenol | 4 | | −3 |
| 2,2-bis(4-hydroxyphenyl)propanoic acid | 5 | | less than −4 |
| 4,4'-methylenebis(2,6-dimethylphenol) | 6 | | less than −4 |
| 4,4'-butylidenebis(2-t-butyl-5-methylphenol) | 7 | | less than −4 |
| 4,4'-methylenebis(2,6-di-t-butylphenol) | 8 | | less than −4 |
| 2,2'-methylenebis(4-methyl-6-t-butylphenol) | 9 | | less than −4 |

TABLE 1-continued

| Polyhydric Compound of Formula II | Structure | Reference Compound | Log RPE |
|---|---|---|---|
| 4,4'-(1,4-phenylenebis(propane-2,2-diyl))diphenol | 10 | | less than −4 |
| 2,2'methylenebis(phenol) | 11 | | less than −4 |
| 2,5-di-t-butylhydroquinone | 12 | | less than −4 |
| 2,2'-Methylenebis(6-(1-methylcyclohexyl)-4-methylphenol | 13 | | less than −4 |
| 2,2'-Methylenebis(6-t-butyl-4-methylphenol) | 14 | | less than −4 |
| 2,2'Methylenebis(4-ethyl-6-t-butylphenol) | 15 | | less than −4 |

Structures 1 through 16 as identified in Table 1 are also shown below:

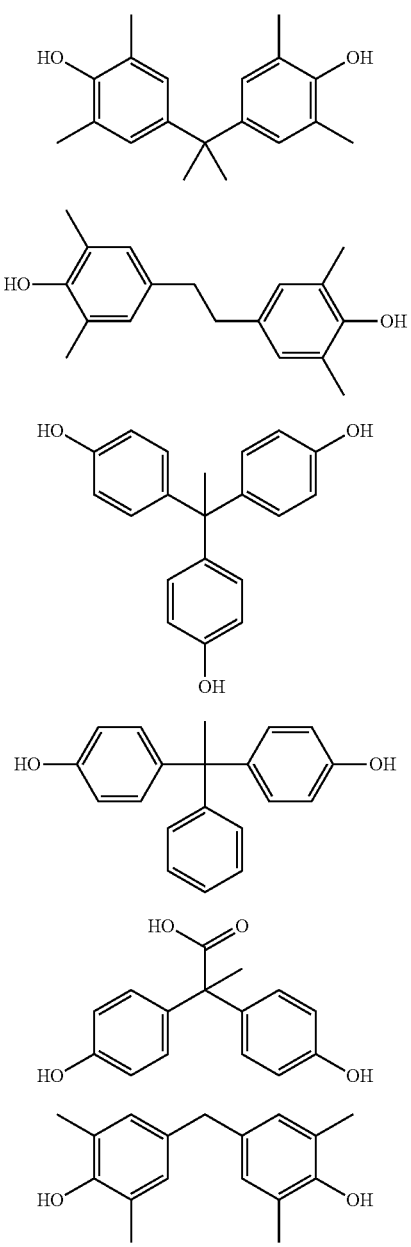
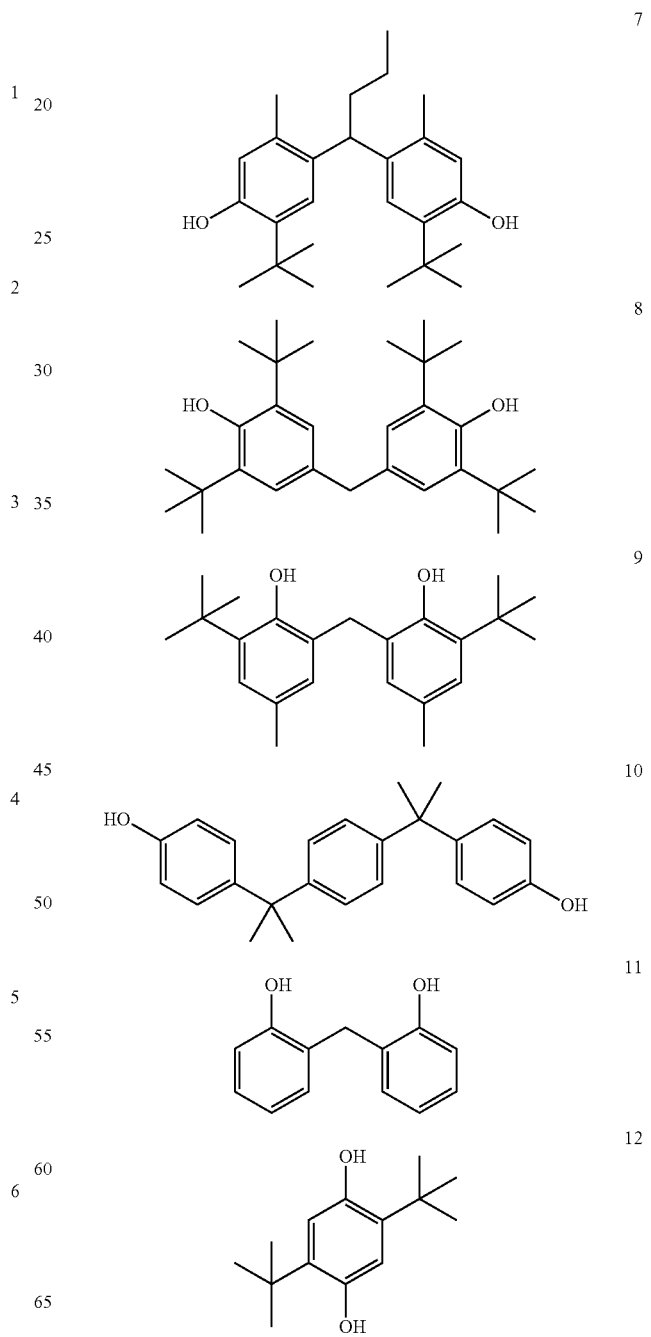

-continued

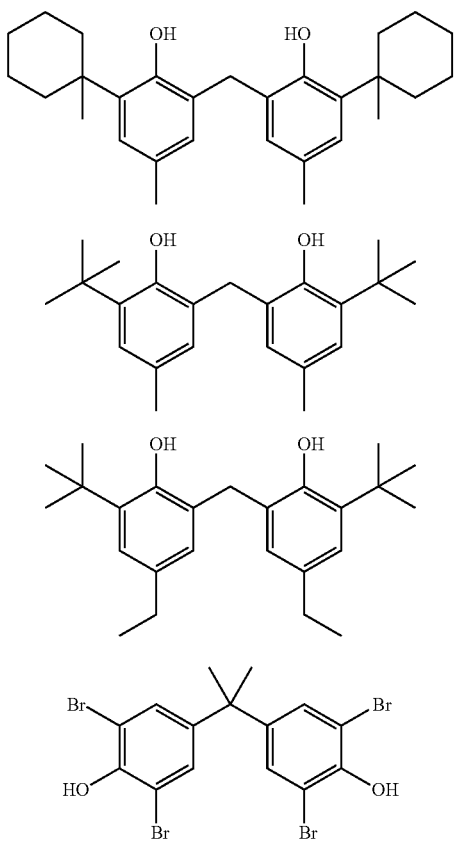

Compounds having no appreciable estrogenic activity may be beneficial in the event that any unreacted, residual compound may be present in the cured dental material. While the balance of scientific data does not indicate that the presence in a resin of very small amounts of residual compounds having estrogenic activity (e.g. as measured in an in vitro recombinant cell assay) pose a human health concern, the use of compounds having no appreciable estrogenic activity in such an assay may nonetheless be desirable from a public perception standpoint. Thus, in preferred embodiments, the disclosed resin is preferably formed using polyhydric phenol compounds of Formula II or compounds containing segments of Formula I that do not exhibit appreciable estrogenic activity in the MCF-7 test.

While not intending to be bound by theory, as previously discussed, it is believed that the presence of substituent groups (e.g., a group other than a hydrogen atom) at one or more of the ortho or meta positions of each phenylene ring of the Formula II compound, relative to the phenol hydroxyl group of each ring, can reduce or effectively eliminate any estrogenic activity. It is believed that the inhibition/elimination of estrogenic activity may be attributable to one or more of the following: (a) steric hindrance of the phenol hydroxyl group (which may cause the overall polyhydric phenol structure to be sufficiently different from estrogenically active compounds such as diethylstilbestrol), (b) the compound having an increased molecular weight due to the presence of the one or more substituent groups, (c) the presence of polar groups or (d) the presence of ortho hydroxyl groups relative to $R^2$. Substitution at one or both of the ortho positions of each phenylene ring is presently preferred for certain embodiments as it is believed that ortho substitution can provide the greatest steric hindrance for the hydroxyl group.

As previously discussed, structural features other than the presence of suitable $R^1$ groups (e.g., features such as (b), (c), and (d) of the preceding paragraph) are believed to inhibit/eliminate estrogenic activity, even in the absence of any $R^1$ groups.

It is believed that molecular weight may be a structural characteristic pertinent to whether a polyhydric phenol is appreciably non-estrogenic. For example, while not intending to be bound by theory, it is believed that if a sufficient amount of relatively "densely" packed molecular weight is present in a polyhydric phenol, it can prevent the compound from being able to fit into the active site of an estrogen receptor (irrespective of whether the polyhydric phenol includes any ortho or meta $R^1$ groups).

The presence of one or more polar groups on the polyhydric phenol compounds of Formula II may be beneficial in making certain embodiments of the disclosed resins, particularly certain embodiments of Formula IIA. The polar groups may be located at any suitable location of the compounds of Formula II, including in $R^1$— or $R^2$. Suitable polar groups may include ketone, carboxyl, carbonate, hydroxyl, phosphate, sulfoxide, and the like, any other polar groups disclosed herein, and combinations thereof.

The below compounds of Formula II may also be used to make certain embodiments of the disclosed resins if desired.

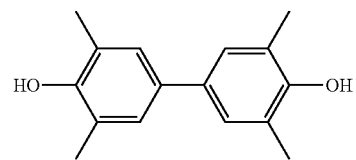

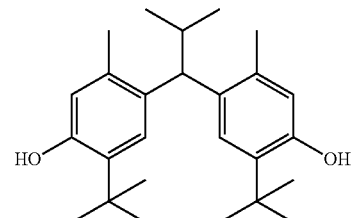

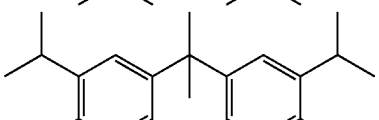

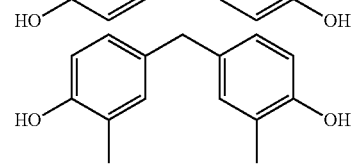

The below compounds are not presently preferred, but may be used to make certain embodiments, if desired.

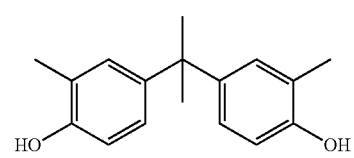

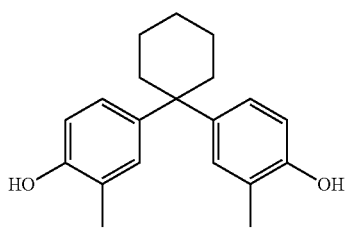

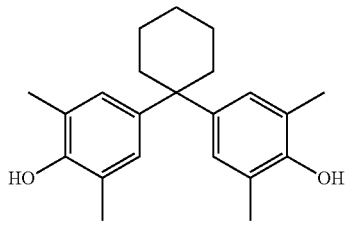

Additional polyhydric phenol compounds that may have utility in making the free radically polymerizable resin are provided below. While the diphenol structures listed below are not "hindered" in the sense of having bulky substituent groups at one or more ortho or meta positions of the phenylene ring(s), it is contemplated that each of the below polyhydric phenol structures may be used in place of, or in addition to, the compounds of Formula II. Such compounds are believed to be appreciably non-estrogenic for one or more of the reasons previously described herein.

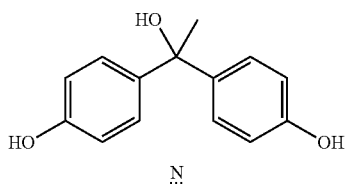

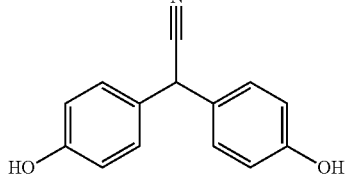

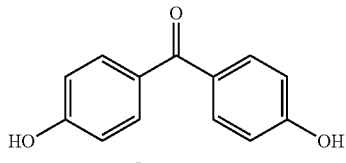

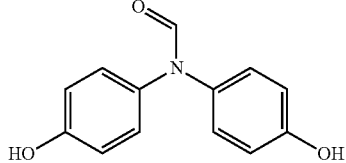

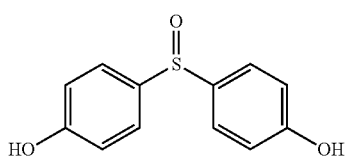

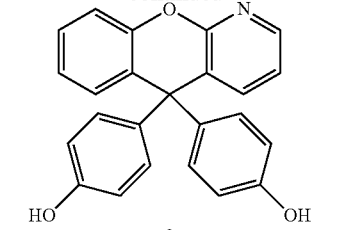

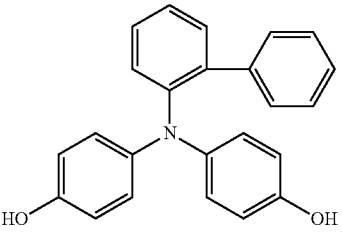

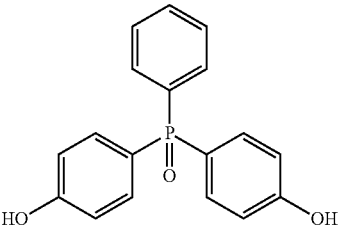 [SMILES: O=P(c1ccccc1)(c1ccc(O)cc1)c1ccc(O)cc1]

Segments of Formula I and compounds of Formula II wherein each of the depicted phenylene groups include one or two ortho $R^1$ groups (relative to the depicted oxygen atom) are presently preferred for making the disclosed resins. To further illustrate such structures, Table 2 shown below exemplifies some non-limiting combinations of one or more ortho $R^1$ and $R^2$, if present, for a given phenylene group. Table 2 is non-limiting with respect to the ring position of $R^2$ (e.g., ortho, meta, para), although typically $R^2$, if present, will be located at a para position relative to the oxygen atom. The columns labeled "Ortho Position A" and "Ortho Position B" indicate the $R^1$ group present at each ortho position of the phenylene group (assuming $R^2$ is not located at an ortho position). Positions "A" or "B" can be either ortho position relative to the depicted oxygen atom. If $R^2$ is located at an ortho position of the phenylene group, then the group listed in the "Ortho Position B" column is not present. Typically, though not required, the phenylene groups in a given segment of Formula I or compound of Formula II will be "symmetric" relative to the second phenylene group such that the same ortho group (as delineated in the ortho position column "A" or "B") is located on each ring at the same ortho position.

Table 2 is also intended as a listing of independent examples of $R^1$ or $R^2$, as well as examples of combinations of $R^1$ and $R^2$ (regardless of whether $R^1$ is ortho or meta relative to the oxygen atom, whether other $R^1$ are present in a particular phenylene group, or whether the one or more $R^1$ are the same for both of the phenylene groups).

TABLE 2

| Ortho Position "A" | Ortho Position "B" | $R^2$ |
|---|---|---|
| Butyl | Hydrogen | 2-Butylidene |
| Butyl | Methyl | 2-Butylidene |
| Butyl | Ethyl | 2-Butylidene |
| Butyl | Propyl | 2-Butylidene |
| Butyl | isopropyl | 2-Butylidene |
| Butyl | Butyl | 2-Butylidene |
| Ethyl | Hydrogen | 2-Butylidene |
| Ethyl | Methyl | 2-Butylidene |

TABLE 2-continued

| Ortho Position "A" | Ortho Position "B" | $R^2$ |
|---|---|---|
| Ethyl | Ethyl | 2-Butylidene |
| Isopropyl | Hydrogen | 2-Butylidene |
| Isopropyl | Methyl | 2-Butylidene |
| Isopropyl | Ethyl | 2-Butylidene |
| Isopropyl | Propyl | 2-Butylidene |
| Isopropyl | isopropyl | 2-Butylidene |
| Methyl | Hydrogen | 2-Butylidene |
| Methyl | Methyl | 2-Butylidene |
| Propyl | Hydrogen | 2-Butylidene |
| Propyl | Methyl | 2-Butylidene |
| Propyl | Ethyl | 2-Butylidene |
| Propyl | Propyl | 2-Butylidene |
| sec-Butyl | Hydrogen | 2-Butylidene |
| sec-Butyl | Methyl | 2-Butylidene |
| sec-Butyl | Ethyl | 2-Butylidene |
| sec-Butyl | Propyl | 2-Butylidene |
| sec-Butyl | isopropyl | 2-Butylidene |
| sec-Butyl | Butyl | 2-Butylidene |
| sec-Butyl | sec-Butyl | 2-Butylidene |
| tert-Butyl | Hydrogen | 2-Butylidene |
| tert-Butyl | Methyl | 2-Butylidene |
| tert-Butyl | Ethyl | 2-Butylidene |
| tert-Butyl | Propyl | 2-Butylidene |
| tert-Butyl | isopropyl | 2-Butylidene |
| tert-Butyl | Butyl | 2-Butylidene |
| tert-Butyl | sec-Butyl | 2-Butylidene |
| tert-Butyl | tert-Butyl | 2-Butylidene |
| Butyl | Hydrogen | Butylene |
| Butyl | Methyl | Butylene |
| Butyl | Ethyl | Butylene |
| Butyl | Propyl | Butylene |
| Butyl | isopropyl | Butylene |
| Butyl | Butyl | Butylene |
| Ethyl | Hydrogen | Butylene |
| Ethyl | Methyl | Butylene |
| Ethyl | Ethyl | Butylene |
| Isopropyl | Hydrogen | Butylene |
| Isopropyl | Methyl | Butylene |
| Isopropyl | Ethyl | Butylene |
| Isopropyl | Propyl | Butylene |
| Isopropyl | isopropyl | Butylene |
| Methyl | Hydrogen | Butylene |
| Methyl | Methyl | Butylene |
| Propyl | Hydrogen | Butylene |
| Propyl | Methyl | Butylene |
| Propyl | Ethyl | Butylene |
| Propyl | Propyl | Butylene |
| sec-Butyl | Hydrogen | Butylene |
| sec-Butyl | Methyl | Butylene |
| sec-Butyl | Ethyl | Butylene |
| sec-Butyl | Propyl | Butylene |
| sec-Butyl | isopropyl | Butylene |
| sec-Butyl | Butyl | Butylene |
| sec-Butyl | sec-Butyl | Butylene |
| tert-Butyl | Hydrogen | Butylene |
| tert-Butyl | Methyl | Butylene |
| tert-Butyl | Ethyl | Butylene |
| tert-Butyl | Propyl | Butylene |
| tert-Butyl | isopropyl | Butylene |
| tert-Butyl | Butyl | Butylene |
| tert-Butyl | sec-Butyl | Butylene |
| tert-Butyl | tert-Butyl | Butylene |
| Butyl | Hydrogen | Ethylidene |
| Butyl | Methyl | Ethylidene |
| Butyl | Ethyl | Ethylidene |
| Butyl | Propyl | Ethylidene |
| Butyl | isopropyl | Ethylidene |
| Butyl | Butyl | Ethylidene |
| Ethyl | Hydrogen | Ethylidene |
| Ethyl | Methyl | Ethylidene |
| Ethyl | Ethyl | Ethylidene |
| Isopropyl | Hydrogen | Ethylidene |
| Isopropyl | Methyl | Ethylidene |
| Isopropyl | Ethyl | Ethylidene |
| Isopropyl | Propyl | Ethylidene |
| Isopropyl | isopropyl | Ethylidene |
| Methyl | Hydrogen | Ethylidene |
| Methyl | Methyl | Ethylidene |
| Propyl | Hydrogen | Ethylidene |
| Propyl | Methyl | Ethylidene |
| Propyl | Ethyl | Ethylidene |
| Propyl | Propyl | Ethylidene |
| sec-Butyl | Hydrogen | Ethylidene |
| sec-Butyl | Methyl | Ethylidene |
| sec-Butyl | Ethyl | Ethylidene |
| sec-Butyl | Propyl | Ethylidene |
| sec-Butyl | isopropyl | Ethylidene |
| sec-Butyl | Butyl | Ethylidene |
| sec-Butyl | sec-Butyl | Ethylidene |
| tert-Butyl | Hydrogen | Ethylidene |
| tert-Butyl | Methyl | Ethylidene |
| tert-Butyl | Ethyl | Ethylidene |
| tert-Butyl | Propyl | Ethylidene |
| tert-Butyl | isopropyl | Ethylidene |
| tert-Butyl | Butyl | Ethylidene |
| tert-Butyl | sec-Butyl | Ethylidene |
| tert-Butyl | tert-Butyl | Ethylidene |
| Butyl | Hydrogen | Methylidene |
| Butyl | Methyl | Methylidene |
| Butyl | Ethyl | Methylidene |
| Butyl | Propyl | Methylidene |
| Butyl | isopropyl | Methylidene |
| Butyl | Butyl | Methylidene |
| Ethyl | Hydrogen | Methylidene |
| Ethyl | Methyl | Methylidene |
| Ethyl | Ethyl | Methylidene |
| Isopropyl | Hydrogen | Methylidene |
| Isopropyl | Methyl | Methylidene |
| Isopropyl | Ethyl | Methylidene |
| Isopropyl | Propyl | Methylidene |
| Isopropyl | isopropyl | Methylidene |
| Methyl | Hydrogen | Methylidene |
| Methyl | Methyl | Methylidene |
| Propyl | Hydrogen | Methylidene |
| Propyl | Methyl | Methylidene |
| Propyl | Ethyl | Methylidene |
| Propyl | Propyl | Methylidene |
| sec-Butyl | Hydrogen | Methylidene |
| sec-Butyl | Methyl | Methylidene |
| sec-Butyl | Ethyl | Methylidene |
| sec-Butyl | Propyl | Methylidene |
| sec-Butyl | isopropyl | Methylidene |
| sec-Butyl | Butyl | Methylidene |
| sec-Butyl | sec-Butyl | Methylidene |
| tert-Butyl | Hydrogen | Methylidene |
| tert-Butyl | Methyl | Methylidene |
| tert-Butyl | Ethyl | Methylidene |
| tert-Butyl | Propyl | Methylidene |
| tert-Butyl | isopropyl | Methylidene |
| tert-Butyl | Butyl | Methylidene |
| tert-Butyl | sec-Butyl | Methylidene |
| tert-Butyl | tert-Butyl | Methylidene |
| Butyl | Hydrogen | Propylidene |
| Butyl | Methyl | Propylidene |
| Butyl | Ethyl | Propylidene |
| Butyl | Propyl | Propylidene |
| Butyl | isopropyl | Propylidene |
| Butyl | Butyl | Propylidene |
| Ethyl | Hydrogen | Propylidene |
| Ethyl | Methyl | Propylidene |
| Ethyl | Ethyl | Propylidene |
| Isopropyl | Hydrogen | Propylidene |
| Isopropyl | Methyl | Propylidene |
| Isopropyl | Ethyl | Propylidene |
| Isopropyl | Propyl | Propylidene |
| Isopropyl | isopropyl | Propylidene |
| Methyl | Hydrogen | Propylidene |
| Methyl | Methyl | Propylidene |
| Propyl | Hydrogen | Propylidene |
| Propyl | Methyl | Propylidene |
| Propyl | Ethyl | Propylidene |
| Propyl | Propyl | Propylidene |
| sec-Butyl | Hydrogen | Propylidene |
| sec-Butyl | Methyl | Propylidene |
| sec-Butyl | Ethyl | Propylidene |
| sec-Butyl | Propyl | Propylidene |

TABLE 2-continued

| Ortho Position "A" | Ortho Position "B" | R² |
|---|---|---|
| sec-Butyl | isopropyl | Propylidene |
| sec-Butyl | Butyl | Propylidene |
| sec-Butyl | sec-Butyl | Propylidene |
| tert-Butyl | Hydrogen | Propylidene |
| tert-Butyl | Methyl | Propylidene |
| tert-Butyl | Ethyl | Propylidene |
| tert-Butyl | Propyl | Propylidene |
| tert-Butyl | isopropyl | Propylidene |
| tert-Butyl | Butyl | Propylidene |
| tert-Butyl | sec-Butyl | Propylidene |
| tert-Butyl | tert-Butyl | Propylidene |
| Butyl | Hydrogen | 1-Phenylethylidene |
| Butyl | Methyl | 1-Phenylethylidene |
| Butyl | Ethyl | 1-Phenylethylidene |
| Butyl | Propyl | 1-Phenylethylidene |
| Butyl | isopropyl | 1-Phenylethylidene |
| Butyl | Butyl | 1-Phenylethylidene |
| Ethyl | Hydrogen | 1-Phenylethylidene |
| Ethyl | Methyl | 1-Phenylethylidene |
| Ethyl | Ethyl | 1-Phenylethylidene |
| Isopropyl | Hydrogen | 1-Phenylethylidene |
| Isopropyl | Methyl | 1-Phenylethylidene |
| Isopropyl | Ethyl | 1-Phenylethylidene |
| Isopropyl | Propyl | 1-Phenylethylidene |
| Isopropyl | isopropyl | 1-Phenylethylidene |
| Methyl | Hydrogen | 1-Phenylethylidene |
| Methyl | Methyl | 1-Phenylethylidene |
| Propyl | Hydrogen | 1-Phenylethylidene |
| Propyl | Methyl | 1-Phenylethylidene |
| Propyl | Ethyl | 1-Phenylethylidene |
| Propyl | Propyl | 1-Phenylethylidene |
| sec-Butyl | Hydrogen | 1-Phenylethylidene |
| sec-Butyl | Methyl | 1-Phenylethylidene |
| sec-Butyl | Ethyl | 1-Phenylethylidene |
| sec-Butyl | Propyl | 1-Phenylethylidene |
| sec-Butyl | isopropyl | 1-Phenylethylidene |
| sec-Butyl | Butyl | 1-Phenylethylidene |
| sec-Butyl | sec-Butyl | 1-Phenylethylidene |
| tert-Butyl | Hydrogen | 1-Phenylethylidene |
| tert-Butyl | Methyl | 1-Phenylethylidene |
| tert-Butyl | Ethyl | 1-Phenylethylidene |
| tert-Butyl | Propyl | 1-Phenylethylidene |
| tert-Butyl | isopropyl | 1-Phenylethylidene |
| tert-Butyl | Butyl | 1-Phenylethylidene |
| tert-Butyl | sec-Butyl | 1-Phenylethylidene |
| tert-Butyl | tert-Butyl | 1-Phenylethylidene |
| Butyl | Hydrogen | Diphenylmethylidene |
| Butyl | Methyl | Diphenylmethylidene |
| Butyl | Ethyl | Diphenylmethylidene |
| Butyl | Propyl | Diphenylmethylidene |
| Butyl | isopropyl | Diphenylmethylidene |
| Butyl | Butyl | Diphenylmethylidene |
| Ethyl | Hydrogen | Diphenylmethylidene |
| Ethyl | Methyl | Diphenylmethylidene |
| Ethyl | Ethyl | Diphenylmethylidene |
| Isopropyl | Hydrogen | Diphenylmethylidene |
| Isopropyl | Methyl | Diphenylmethylidene |
| Isopropyl | Ethyl | Diphenylmethylidene |
| Isopropyl | Propyl | Diphenylmethylidene |
| Isopropyl | isopropyl | Diphenylmethylidene |
| Methyl | Hydrogen | Diphenylmethylidene |
| Methyl | Methyl | Diphenylmethylidene |
| Propyl | Hydrogen | Diphenylmethylidene |
| Propyl | Methyl | Diphenylmethylidene |
| Propyl | Ethyl | Diphenylmethylidene |
| Propyl | Propyl | Diphenylmethylidene |
| sec-Butyl | Hydrogen | Diphenylmethylidene |
| sec-Butyl | Methyl | Diphenylmethylidene |
| sec-Butyl | Ethyl | Diphenylmethylidene |
| sec-Butyl | Propyl | Diphenylmethylidene |
| sec-Butyl | isopropyl | Diphenylmethylidene |
| sec-Butyl | Butyl | Diphenylmethylidene |
| sec-Butyl | sec-Butyl | Diphenylmethylidene |
| tert-Butyl | Hydrogen | Diphenylmethylidene |
| tert-Butyl | Methyl | Diphenylmethylidene |
| tert-Butyl | Ethyl | Diphenylmethylidene |
| tert-Butyl | Propyl | Diphenylmethylidene |
| tert-Butyl | isopropyl | Diphenylmethylidene |
| tert-Butyl | Butyl | Diphenylmethylidene |
| tert-Butyl | sec-Butyl | Diphenylmethylidene |
| tert-Butyl | tert-Butyl | Diphenylmethylidene |

The disclosed polyhydric phenols such as those of Formula II, or compounds containing segments such as those of Formula I, may be used to make the disclosed free-radically polymerizable resins by reacting the polyhydric phenol or compound to impart one or more and preferably two free-radically active functional groups (e.g., ethylenically unsaturated groups) into the resin. Acrylate- or methacrylate-functional free-radically polymerizable resins are especially preferred. A preferred method for making such resins involves reacting a polyhydric phenol with glycidyl(meth) acrylate by adapting the procedures described in the above-mentioned U.S. Pat. No. 3,066,112 to Bowen. The disclosed resins may include (meth)acrylate functionality and epoxy functionality, and if so may be made by adapting the procedures described in the above-mentioned U.S. Patent Application Publication No. US 2006/0009540 A1 to Jia et al.

The disclosed resins may also be made by converting a polyhydric phenol (preferably a dihydric phenol) containing a segment or segments of Formula I to a polyepoxide (preferably a diepoxide), and then reacting the oxirane groups in the polyepoxide with (meth)acrylic acid to form ethylenically unsaturated free-radically polymerizable end groups. The oxirane groups in the polyepoxide may be attached via any suitable linkage, including, for example, ether-containing or ester-containing linkages. Glycidyl ethers of polyhydric phenols and glycidyl esters of polyhydric phenols are preferred polyepoxides, with diglycidyl ethers being particularly preferred.

An exemplary polyepoxide compound containing segments of Formula I is depicted in Formula III below:

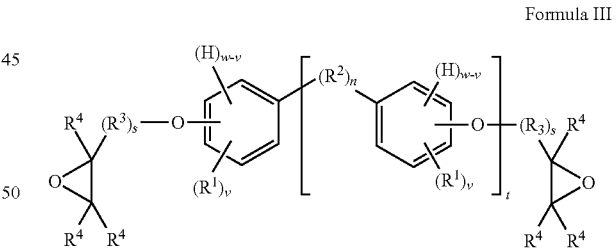

Formula III wherein:

H, $R^1$, $R^2$, n, t, v, and w are as described above for Formula I;

s is 0 to 1, more preferably 1;

Each $R^3$, if present, is independently a divalent group, more preferably a divalent organic group; and preferably each $R^4$ is independently a hydrogen atom, a halogen atom, or a hydrocarbon group that may include one or more heteroatoms; and more preferably each $R^4$ is a hydrogen atom.

When t is 1, the polyepoxide of Formula III has Formula IIIA below:

Formula IIIA

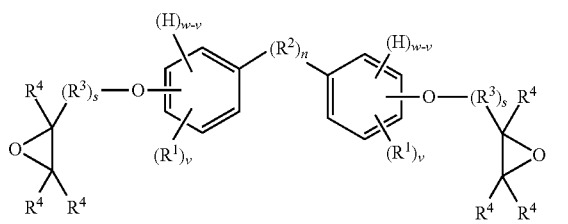

When t is 0, the polyepoxide of Formula III has Formula IIIB below:

Formula IIIB

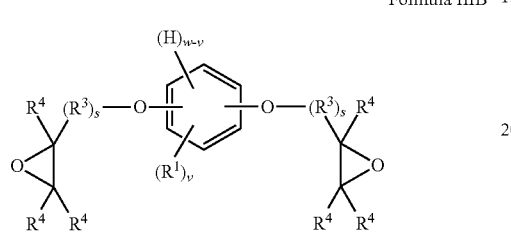

$R^3$ is typically a hydrocarbyl group, which may optionally include one or more heteroatoms. Preferred hydrocarbyl groups include groups having from one to four carbon atoms, with methylene groups being particularly preferred. In some embodiments, $R^3$ includes a carbonyl group. In one such embodiment, $R^3$ includes a carbonyl group that is attached to the oxygen atom depicted in Formula III (e.g., as in an ester linkage).

Preferred polyepoxide compounds of Formula III are non-mutagenic, more preferably non-genotoxic. A useful test for assessing both mutagenicity and genotoxicity is the mammalian in vivo assay known as the in vivo alkaline single cell gel electrophoresis assay (referred to as the "comet" assay). The method is described in Tice, R. R. "The single cell gel/comet assay: a microgel electrophoretic technique for the detection of DNA damage and repair in individual cells." *Environmental Mutagenesis*. Eds. Phillips, D. H. and Venitt, S. Bios Scientific, Oxford, UD, 1995, pp. 315-339. A negative test result in the comet assay indicates that a compound is non-genotoxic and, therefore, non-mutagenic, though a positive test does not definitively indicate the opposite and in such cases a more definitive test may be utilized (e.g., a two-year rat feeding study).

If t of Formula III is 0, v is preferably 1 or more, more preferably 2 or more.

While not intending to be bound by theory, it is believed that the presence of one or more $R^1$ groups, and particularly one or more ortho $R^1$ groups, can contribute to the diepoxide of Formula IIIB being non-genotoxic.

In one embodiment, epichlorohydrin may be used to form a diepoxide of Formula III. By way of example, below is a diepoxide formed via an epichlorohydrin epoxidation of 4,4'-methylenebis(2,6-di-t-butylphenol).

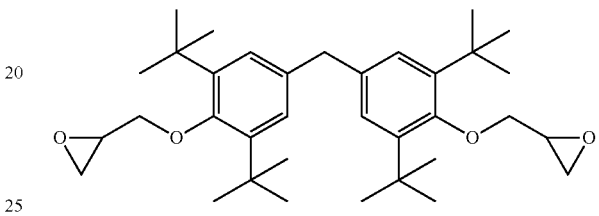

In another embodiment, epichlorohydrin may be used to form a diepoxide of Formula III, and the resulting diepoxide may be reacted with an ethylenically-unsaturated acid or acid anhydride to provide a resin with ethylenically unsaturated free-radically polymerizable groups. By way of example, Formula IV below is a resin formed by epichlorohydrin epoxidation to form a diepoxide of Formula III followed by reaction with a (meth)acrylic acid:

Formula IV

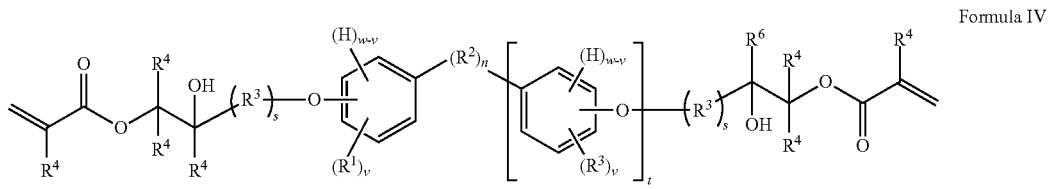

wherein:
$R^1$, $R^2$, n, t, v, and w are as described above for Formula I; and
$R^3$, $R^4$ and s are as described above for Formula III.

By way of further example, Formula V below is a resin formed by epichlorohydrin epoxidation to form a diepoxide of Formula III followed by reaction with an anhydride such as maleic anhydride:

Formula V

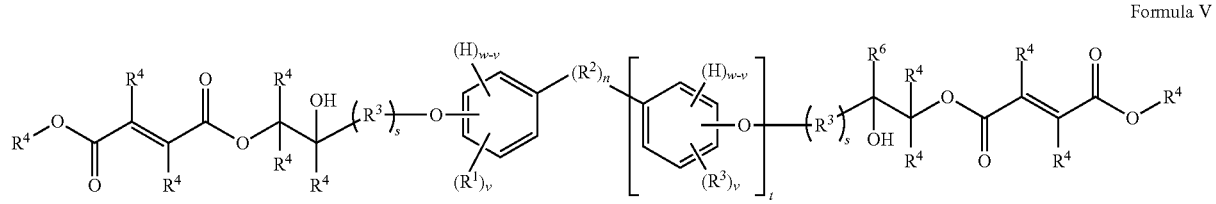

wherein:
R$^1$, R$^2$, n, t, v, and w are as described above for Formula I; and
R$^3$, R$^4$ and s are as described above for Formula III.

In another embodiment, a polyhydric phenol of Formula II may be reacted with a suitable difunctional linking compound, followed by reacting (e.g., end-capping) the resulting product with a suitable ethylenically unsaturated compound. By way of Example, Formula VI below is a resin formed by reacting a polyhydric phenol of Formula II with a linking compound containing Z segments and then reacting the resulting product with an ethylenically unsaturated compound containing R$^{11}$ and R$^{12}$ groups:

Formula VI

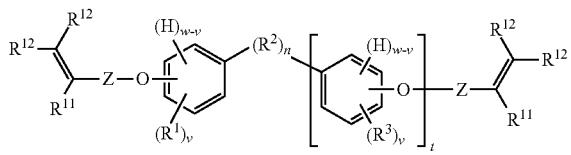

wherein:
R$^1$, R$^2$, n, t, v, and w are as described above for Formula I;
Each Z is a divalent linking group containing for example less than 20, less than 10 or less than 5 carbon atoms; and
Each R$^{11}$ and R$^{12}$ are independently hydrogen atoms, halogen atoms, or alkyl groups that may include one or more heteroatoms; and more preferably R$^{11}$ and R$^{12}$ are all hydrogen atoms.

The disclosed dental materials may include optional diluents, e.g., reactive diluent monomers. Diluent monomers may be used to increase the surface wettability or decrease the viscosity of the disclosed dental materials. Exemplary diluent monomers include acrylic acid esters, methacrylic acid esters, hydroxy-functional acrylic acid esters, hydroxy-functional methacrylic acid esters, and combinations thereof. Preferred diluent monomers include mono- or multi-functional (meth)acrylate monomers include alkyl (meth)acrylates, cycloalkyl(meth)acrylates, aralkyl(meth)acrylates and 2-hydroxyalkyl(meth)acrylates, such as butane dimethacrylate, dodecane dimethacrylate, 2-hydroxyethyl (meth)acrylate, 2-hydroxypropyl(meth)acrylate, isobornyl (meth)acrylate, butyl glycol(meth)acrylate, acetyl glycol (meth)acrylate, ethylene glycol(meth)acrylate, diethylene glycol(meth)acrylate, tri(ethylene glycol)di(meth)acrylate and tetra(ethylene glycol)di(meth)acrylate, polyethylene glycol di(meth)acrylate, 2-phenylethyl(meth)acrylate, 2-ethylhexyl(meth)acrylate, cyclohexyl(meth)acrylate, lauryl (meth)acrylate, hexanediol di(meth)acrylate, glycerol mono- or di-(meth)acrylate, trimethylolpropane mono- or di-(meth)acrylate, pentaerythritol mono-, di-, and tri-(meth) acrylate, sorbitol mono-, di-, tri-, tetra-, or penta-(meth) acrylate, and mixtures of any such diluent monomers. Tri (ethylene glycol)dimethacrylate (TEGDMA) is particularly preferred. Suitable diluent monomers are available from a wide variety of commercial sources, such as Sigma-Aldrich, St. Louis. Diluent monomers, when present, preferably are incorporated into the disclosed dental materials in an amount of about 1 to about 70 wt % of the total dental material.

The disclosed dental materials may additionally include adjuvants suitable for use in dental materials, such as pigments, flavorants, medicaments, stabilizers, viscosity modifiers, and the like. Such adjuvants may optionally have reactive functionality so that they will be copolymerized with the resin.

Other optional ingredients that do not adversely affect the disclosed dental materials or a cured dental restoration resulting therefrom may be included to enhance esthetics; to facilitate manufacturing, processing, handling, and application of the dental material; or to further improve a particular functional property of a dental material or a cured dental restoration resulting therefrom. For example, the disclosed dental materials may optionally include crosslinkers, catalysts, lubricants, surfactants, coalescents, extenders, flow control agents, thixotropic agents, dispersing agents, antioxidants, adhesion promoters, and mixtures thereof, as required to provide the desired properties. Each optional ingredient is preferably included in a sufficient amount to serve its intended purpose, but not in such an amount as to adversely affect the dental material or a cured dental restoration resulting therefrom.

Preferred dental materials are substantially free of mobile BPA and BADGE, and more preferably essentially free of these compounds, and most preferably completely free of these compounds. The dental material is also preferably substantially free of bound BPA and BADGE, more preferably essentially free of these compounds, and optimally completely free of these compounds. In addition, preferred materials are also substantially free, more preferably essentially free, and most preferably completely free of bisphenol S, bisphenol F, and the diglycidyl ether of bisphenol F or bisphenol S.

The disclosed dental materials may be used with additional materials, such as inlays, onlays and the like, or may act as the filling material itself if applied and cured in one or more layers. The disclosed dental materials also find utility as a cured article for subsequent placement in the mouth as a prosthetic device. Examples of such devices include crowns, bridges, inlays, onlays, implants and general formats that may be further fabricated or shaped into the desired final product for placement in the oral environment.

The invention is further illustrated in the following non-limiting examples. Unless otherwise indicated, all parts and percentages are by weight.

EXAMPLES

Example 1

Diepoxides of Ortho-Substituted Polyhydric Phenols psRun I: Diglycidyl ether of 4,4'-methylenebis(2,6-di-tert-butylphenol)

A solution of 4,4'-methylenebis(2,6-di-t-butylphenol) (500 grams, 1.076 moles obtained from Albemarle Corporation) in anhydrous dimethylformamide (1.5 liters) was cooled to −10° C. and a solution of sodium tert-pentoxide (374 grams, 3.23 moles) in anhydrous dimethylformamide (1.5 liters) was added dropwise at −10 to −5° C. The mixture was stirred for 30 minutes at −10° C. Epichlorohydrin (1.9 liters, 24.2 moles) was added via dropping funnel at −10 to −5° C. The solution was allowed to warm up to room temperature and then was heated for 16 hours at a temperature of from 75 to 82° C. After cooling down to ambient temperature, the mixture was added to cold tap water (12 liters). Ethyl acetate (5 liters) was added to the mixture, which was stirred for 10 minutes and separated. The aqueous layer was extracted again with additional ethyl acetate (3 liters). The combined ethyl acetate extracts were washed twice with brine (2 x 6 liters), dried over anhydrous sodium sulfate (600 grams), and filtered. The solvent was removed under reduced pressure to give 887 grams of crude product as a purple oil. The crude product was dissolved in toluene (600 milliliters) and passed over a silica gel pad (1.4 kilograms), and eluted with a mixture of toluene and heptane (8 parts toluene to 2 parts heptane). The fractions containing product were combined and evaporated under reduced pressure. The product was mostly the desired diepoxide (756 grams, yellow oil which crystallizes in time), with some monoepoxide present. The purified material (756 grams) was dissolved at 70° C. in 2-propanol (2.3 liters) and then allowed to cool down to room temperature overnight. The flask was kept in an ice-water bath for 3 hours, filtered and the solids were washed three times with cold 2-propanol (3 x 400 milliliters). The obtained solid was dried under high vacuum at ambient temperature to give the final product as a white solid (371 grams having an HPLC purity of 95.2%, and a yield of 60%). The epoxy value of the final product was 0.367 equivalents per 100 grams. The resulting diglycidyl ether of 4,4'-methylenebis(2,6-di-t-butylphenol) was tested using suitable genotoxicity assays (e.g., an Ames II assay) and was found to be non-genotoxic.

Run II: Diglycidyl ether of 4,4'Butylidenebis(2-t-butyl-5-methylphenol))

A 20-gram batch of the diglycidyl ether of 4,4'-butylidenebis(2-t-butyl-5-methylphenol) was prepared by reacting epichlorohydrin with 4,4'-butylidenebis(2-t-butyl-5-methylphenol). Multiple purification steps were required to obtain a suitably pure batch. The purified batch exhibited an epoxy value of 0.402 equivalents per 100 grams. The resulting diglycidyl ether of 4,4'-butylidenebis(2-t-butyl-5-methylphenol) was tested using suitable genotoxicity assays (e.g., Ames II assay) and was found to be non-genotoxic.

Run III: Diglycidyl ether of 4,4'-methylenebis(2,6-dimethylphenol)

4,4'-Methylenebis(2,6-dimethylphenol) (32 grams, 0.125 moles), epichlorohydrin (140 milliliters, 1.79 moles), and 2-propanol (150 milliliters) were heated to 80° C. in an oil bath. Sodium hydroxide (12.5 grams, 0.313 moles) in water (20 milliliters) was added in portions over 5 minutes. The purple solution was heated for 2 hours at 80° C. The mixture was cooled to room temperature, filtered, and concentrated on a rotary evaporator at a temperature of about 30-40° C. The remaining oil was mixed with dichloromethane (50 milliliters) and heptane (100 milliliters) and allowed to stir for 30 minutes at ambient temperature. The salts were removed by filtration and the filtrate was concentrated on a rotary evaporator at 30-40° C. The remaining oil was dried under high vacuum at ambient temperature until a constant weight was obtained. The crude product was crystallized twice from methanol (250 milliliters) and dried under high vacuum at ambient temperature until a constant weight was obtained. The experiment generated diglycidyl ether of 4,4'-methylenebis(2,6-dimethylphenol) (28 grams, 60% yield) as a white solid. The epoxy value was 0.543 equivalents per 100 grams.

The polyhydric phenols used to make the diglycidyl ethers of each of Runs I-III were assayed for estrogenic activity by an outside toxicology laboratory using a suitable assay whose results are known to be directly correlatable to the MCF-7 assay based on common reference compounds.

Example 2

Preparation of Dental Components

Preparation of Bisphenol A Diglycidyl Methacrylate (Bis-GMA)

Components:

| | |
|---|---|
| EPON ™ 828 diepoxide | 549.8 grams |
| Methacrylic Acid | 248.9 grams |
| BHT (2,6-di-tert-butyl-4-methylphenol) | 0.8 grams |
| N-Benzyldimethylamine | 0.8 grams |
| TEGDMA | 199.7 grams |

The EPON 828 diepoxide and BHT were charged to a 2 liter flask, equipped with a stirrer, a gas inlet, a thermocouple, and a condenser and heated to 108° C. with an air sparge. With the contents of the flask at 108° C., the methacrylic acid was added dropwise into the batch with an addition funnel over the course of two hours and the temperature was maintained at 105° C. throughout the addition. After the addition of the methacrylic acid was complete, the batch was held at temperature for 15 minutes, then the N-benzyldimethylamine was added. The batch was then held at 105° C. for about 11.5 hours, at which point the acid value had reached 13 mg KOH/gram. At this point, an additional 0.8 grams of N-benzyldimethylamine and 0.8 grams of BHT were added to the batch and it was held at 105° C. for an additional 9.5 hours after which the acid value was 6.7 mg of KOH/gram. The TEGDMA was then added to the flask and the contents were cooled and poured into a container.

Preparation of Butylidene Diglycidyl Ether Dimethacrylic Acid (BUDGE-DMA)

Components:

| | |
|---|---|
| Butylidine diglycidyl ether (from Example 1, Run II) | 150.3 grams |
| Methacrylic acid | 49.7 grams |
| BHT | 0.2 grams |
| N-benzyldimethylamine | 0.7 grams |
| TEGDMA | 50.0 grams |

The butylidine diglycidyl ether was charged to a flask equipped with a stirrer, a gas inlet, a thermocouple, and a condenser and heated to 105° C. with an air sparge. With the contents of the flask at 105° C., a mixture of the methacrylic acid, BHT, and N-benzyldimethylamine was fed into the flask dropwise over about 75 minutes, after which the contents of the flask were held at 105° C. for about 20 hours and a final acid value of 0.5 mg KOH/gram was obtained. The contents of the flask were then cooled to 85° C. and the TEGDMA was added. The batch was then cooled and poured.

Materials:

TEGDMA was obtained from Sartomer, USA, LLC Exton, Pa.

Camphorquinone, diphenyliodonium hexafluorophosphate, BHT, N-benzyldimethylamine, methacrylic acid, and dimethyl amino phenethanol were obtained from Sigma-Aldrich Corp., St. Louis, Mo.

EPON 828 was obtained from Momentive, Columbus, Ohio

Example 3

Dental Materials

Dental materials were prepared by mixing the ingredients shown in Table 3:

TABLE 3

| Comparison Dental Material A (no filler) | |
|---|---|
| 10.0 g | BIS-GMA (prepared in Example 2) |
| 6.0 g | TEGDMA |
| 0.08 g | Camphorquinone |
| 0.08 g | Diphenyliodonium hexafluorophosphate |
| 0.08 g | Dimethyl amino phenethanol |
| Dental Material 1 (no filler) | |
| 10.0 g | BUDGE-DMA (prepared in Example 2) |
| 6.0 g | TEGDMA |
| 0.08 g | Camphorquinone |
| 0.08 g | Diphenyliodonium hexafluorophosphate |
| 0.08 g | Dimethyl amino phenethanol |
| Comparison Dental Material B (with filler) | |
| 10.0 g | BIS-GMA (prepared in Example 2) |
| 6.0 g | TEGDMA |
| 9.29 g | Crystalline silica (IMSIL A-10) |
| 0.08 g | Camphorquinone |
| 0.08 g | Diphenyliodonium hexafluorophosphate |
| 0.08 g | Dimethyl amino phenethanol |
| Dental Material 2 (with filler) | |
| 10.0 g | BUDGE-DMA (prepared in Example 2) |
| 6.0 g | TEGDMA |
| 9.29 g | Crystalline silica (IMSIL A-10, from Unimin Corp., Elco, IL.) |
| 0.08 g | Camphorquinone |
| 0.08 g | Diphenyliodonium hexafluorophosphate |
| 0.08 g | Dimethyl amino phenethanol |

The above compositions were then formed into bars as follows: upon the platen glass of a 3M™ overhead projector (from 3M Company), a thin polyethylene film was secured using adhesive tape. Two microscope slides were affixed to the plastic in a parallel gapped orientation using adhesive tape. The distance between the two slides was slightly less than one slide width in the plane of the slides. Next, a polyethylene film was affixed to a third microscope slide using a thin grease film. Then, the above compositions were poured between the two slides on the projector and the third slide was laid across the other two in such a way that it bridged the gap between them and was arranged perpendicular to the first two slides. The slide was firmly pressed down to squeeze out excess material, creating a polymerizable bar between the slides. The overhead projector was then turned on to cure the materials. Cure time was 60 seconds for clear materials and 120 seconds for filled materials.

After curing, the bars were trimmed to a regular rectangular shape by scoring with a razor blade and breaking off the excess material. The resulting bars were approximately 60-70 mms in length, 6-12 mm in width and approximately 1 mm thick. A dynamic mechanical analyzer was used to study the materials at about 25° C. temperature and a frequency of 1 Hz at 0.5% strain Pascal. The results shown below in Table 4 are the Storage Modulus (G') reported in Pascals (Pa).

TABLE 4

| Sample | Storage Modulus (G') at Room Temperature and 1 Hz at 0.5% strain (Pa) | | | | G' (Pa) Average | G' (Pa) Std Dev |
|---|---|---|---|---|---|---|
| | 1 | 2 | 3 | 4 | | |
| Comparison Material A | 2.45E+09 | 2.23E+09 | | | 2.34E+09 | 1.54E+08 |
| Comparison Material B | 5.61E+09 | 5.08E+09 | 4.57E+09 | 5.99E+09 | 5.31E+09 | 6.21E+08 |
| Dental Material 1 | 1.66E+09 | 1.89E+09 | 1.92E+09 | 1.29E+09 | 1.69E+09 | 2.92E+08 |
| Dental Material 2 | 3.94E+09 | 4.49E+09 | 4.38E+09 | 4.42E+09 | 4.31E+09 | 2.52E+08 |

The results show Dental Material 1 and Dental Material 2 have mechanical properties comparable to those of conventional BPA-derived dental materials but with resins that are substantially free of polyhydric phenols having estrogenic activity greater than or equal to that of BPS.

Examples 4-12

In the same manner as the BUDGE-DMA was prepared in Example 2, additional resins may be prepared by replacing the BUDGE-DMA with the polyhydric phenols shown below in Table 5:

TABLE 5

| Example | Polyhydric Phenol |
|---|---|
| Comparison Example C | Bisphenol S |
| Example 4 | 4,4'-(propane-2,2-diyl)bis(2,6-dimethylphenol) |
| Example 5 | 4,4'-methylenebis(2,6-dimethylphenol) |
| Example 6 | 4,4'-(ethane-1,2-diyl)bis(2,6-dimethylphenol) |
| Example 7 | 4,4'-butylidenebis(2-t-butyl-5-methylphenol) |
| Example 8 | 4,4'-methylenebis(2,6-di-t-butylphenol) |
| Example 9 | 2,2'-methylenebis(4-methyl-6-t-butylphenol) |
| Example 10 | 4,4'-(ethane-1,2-diyl)bis(2,6-dimethylphenol) |
| Example 11 | Tetrabromobisphenol A |
| Example 12 | 2,5-di-t-butylhydroquinone |

The resulting resins may show mechanical properties comparable to those of conventional BPA-derived dental materials but with resins that are substantially free of polyhydric phenols having estrogenic activity greater than or equal to that of BPS.

All patents, patent applications and literature cited in the specification are hereby incorporated by reference in their entirety. In the case of any inconsistencies, the present disclosure, including any definitions therein will prevail. The invention has been described with reference to various specific and preferred embodiments and techniques. However, it should be understood that many variations and modifications may be made while remaining within the invention.

The invention claimed is:

1. A dental material comprising:
   a free-radical polymerization initiator; and
   a free-radically-polymerizable resin comprising:
   a) at least two ethylenically unsaturated free-radically polymerizable end groups; and
   b) a segment comprising:
   (i) two or more aryl or heteroaryl groups in which each aryl or heteroaryl group includes an oxygen atom attached to the ring and (a) an ethyl, propyl, isopropyl, butyl, sec-butyl, or tert-butyl substituent group attached to the ring at an ortho or meta position relative to the oxygen atom, or (b) two substituent groups attached to the ring at both ortho positions relative to the oxygen atom;
   (ii) and in which two or more aryl or heteroaryl groups are joined by an unsubstituted methylene bridge (—$CH_2$—);
   wherein the polymerizable resin is substantially free of polyhydric phenols having estrogenic activity greater than or equal to that of bisphenol S.

2. A dental material of claim 1, wherein the at least two ethylenically unsaturated free-radically polymerizable end groups comprises one or more (meth)acrylate groups.

3. The dental material of claim 1, wherein the segment has a structure of Formula I:

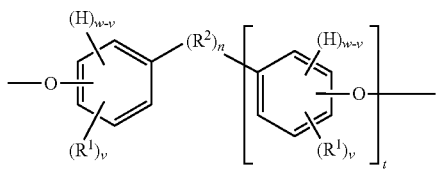

Formula I wherein:
H denotes a hydrogen atom, if present;
each $R^1$ is (a) an ethyl, propyl, isopropyl, butyl, sec-butyl, or tert-butyl substituent group attached to the ring at an ortho or meta position relative to the oxygen atom, or (b) independently an atom or group having an atomic weight of at least 15 Daltons attached to the ring at both ortho positions relative to the oxygen atom;
v is independently 2 to 4;
w is 4;
$R^2$ is a divalent unsubstituted methylene bridge (—$CH_2$—);
n is 1;
t is 1;
two or more $R^1$ groups can join to form one or more cyclic groups, and
the polymerizable resin includes at least two free-radically polymerizable end groups.

4. The dental material of claim 3, wherein the one or more $R^1$ groups independently comprise methyl groups.

5. The dental material of claim 3, wherein each of the phenylene groups depicted in Formula I includes at least one $R^1$ group attached to the phenylene ring at an ortho position relative to the oxygen atom.

6. The dental material of claim 3, wherein each of the phenylene groups depicted in Formula I includes two separate $R^1$ groups attached to the phenylene ring at both ortho positions relative to the oxygen atom.

7. The dental material of claim 3, wherein the one or more $R^1$ groups independently comprise ethyl groups.

8. The dental material of claim 3, wherein an $R^1$ group is attached to the phenylene ring at an ortho position relative to the oxygen atom, and a width measured perpendicular from a centerline of the phenylene ring to the maximal outside extent of the van der Waals volume of $R^1$ is greater than about 4.5 Angstroms.

9. The dental material of claim 3, wherein the oxygen atom of each phenylene group depicted in Formula I is located at a para position relative to: $R^2$.

10. The dental material of claim 1, wherein the free-radically polymerizable resin is derived from one or more of the diglycidyl ether of 4,4'-methylenebis(2,6-di-t-butylphenol), the diglycidyl ether of 2,2'-methylenebis(4-methyl-6-t-butylphenol), the diglycidyl ether of 4,4'-methylenebis(2,6-dimethylphenol) or a derivative or combination thereof.

11. The dental material of claim 1, wherein the dental material is a dental sealant, and further comprises a pigment.

12. The dental material of claim 1, wherein the dental material is a dental composite or dental cement, and further comprises a filler.

13. The dental material of claim 12, containing from about 10-90 wt % of the filler, from about 0.1 to about 5 wt % of the free-radical polymerization initiator and from about 5 to 95 wt % of the free-radically-polymerizable resin.

14. The dental material of claim 1, wherein the segment of the polymerizable resin is derived from a polyhydric phenol or derivative thereof that exhibits a log Relative Proliferative Effect value in an MCF-7 cell proliferation assay less than that of bisphenol S.

15. A method of restoring a tooth comprising:
   applying to the tooth a dental material comprising:
   a free-radical polymerization initiator;
   a filler; and
   a free-radically-polymerizable resin comprising:
   a) at least two ethylenically unsaturated free-radically polymerizable end groups; and
   b) a segment comprising:
   (i) two or more aryl or heteroaryl groups in which each aryl or heteroaryl group includes an oxygen atom attached to the ring and (a) an ethyl, propyl, isopropyl, butyl, sec-butyl, or tert-butyl substituent group attached to the ring at an ortho or meta position relative to the oxygen atom, or (b) two substituent groups attached in both ortho positions relative to the oxygen atom;
   (ii) and in which two or more aryl or heteroaryl groups are joined by an unsubstituted methylene bridge (—$CH_2$—);
   wherein the polymerizable resin is substantially free of polyhydric phenols having estrogenic activity greater than or equal to that of bisphenol S; and
   polymerizing the dental material to form a dental restoration.

16. A method for making a dental material, comprising mixing:
   a) a free-radically-polymerizable resin comprising:
   i) at least two ethylenically unsaturated free-radically polymerizable end groups and
   ii) two or more aryl or heteroaryl ring segments having an oxygen atom attached to the ring and (a) an ethyl, propyl, isopropyl, butyl, sec-butyl, or tert-butyl substituent group attached to the ring at an ortho or meta position relative to the oxygen atom, or (b) two substituent groups attached in both ortho positions relative to the oxygen atom; and in which two or more aryl or heteroaryl ring segments are joined by an unsubstituted methylene bridge (—$CH_2$—);

the resin being substantially free of polyhydric phenols having estrogenic activity greater than or equal to that of bisphenol S:

b) a polymerization initiator; and
c) optionally, a filler.

* * * * *